US011170498B2

United States Patent
Kono et al.

(10) Patent No.: US 11,170,498 B2
(45) Date of Patent: Nov. 9, 2021

(54) IMAGE PROCESSING DEVICE, IMAGE PROCESSING METHOD, AND IMAGE PROCESSING PROGRAM FOR DETECTING SPECIFIC REGION FROM IMAGE CAPTURED BY ENDOSCOPE DESIGNATED AS DETECTION TARGET IMAGE IN RESPONSE TO DETERMINING THAT OPERATOR'S ACTION IN NOT PREDETERMINED ACTION

(71) Applicant: Olympus Corporation, Hachioji (JP)

(72) Inventors: Takashi Kono, Hachioji (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 707 days.

(21) Appl. No.: 15/849,343

(22) Filed: Dec. 20, 2017

(65) Prior Publication Data
US 2018/0114319 A1 Apr. 26, 2018

Related U.S. Application Data

(63) Continuation of application No. PCT/JP2015/068736, filed on Jun. 29, 2015.

(51) Int. Cl.
*G06T 7/00* (2017.01)
*A61B 1/00* (2006.01)
(Continued)

(52) U.S. Cl.
CPC ........ *G06T 7/0012* (2013.01); *A61B 1/00006* (2013.01); *A61B 1/00009* (2013.01);
(Continued)

(58) Field of Classification Search
CPC . A61B 1/00009; A61B 1/00039; A61B 1/015; A61B 1/018; A61B 1/126; G06T 2207/10068; G06T 2207/30032
See application file for complete search history.

(56) References Cited

U.S. PATENT DOCUMENTS

2008/0058593 A1 3/2008 Gu et al.
2008/0108873 A1* 5/2008 Gattani ............. H04N 5/23296
600/168
(Continued)

FOREIGN PATENT DOCUMENTS

JP 2010-512173 4/2010
JP 2012-020028 2/2012
(Continued)

OTHER PUBLICATIONS

English Translation with International Search Report and Written Opinion dated Sep. 29, 2015 issued for PCT/JP2015/068736; 6 Pages.

*Primary Examiner* — John P Leubecker
(74) *Attorney, Agent, or Firm* — Scully, Scott, Murphy & Presser, P.C.

(57) ABSTRACT

An endoscope system includes an endoscope and an image processing device attached to one another. The image processing device includes at least one processor configured to perform operations of determining an operator's action based on an action signal from an endoscope inserted into a subject body, deciding whether an image is set as a detection target image based on the operator's action and detecting a specific region from the detection target image. The processor performs an operation of determining whether the operator's action at a time of capturing the image is a treatment action to give the subject body a treatment. Furthermore, the processor detects, from the image, a region, which exhibits a specular reflection and whose time change in area and (Continued)

position is large, as a washed region and then determine the operator's action at the time of capturing the image is the treatment action when the washed region is detected.

26 Claims, 11 Drawing Sheets

(51) Int. Cl.
    *A61B 1/04*     (2006.01)
    *A61B 1/12*     (2006.01)
    *A61B 1/015*     (2006.01)
    *A61B 1/018*     (2006.01)

(52) U.S. Cl.
    CPC .......... *A61B 1/00039* (2013.01); *A61B 1/015* (2013.01); *A61B 1/018* (2013.01); *A61B 1/04* (2013.01); *A61B 1/126* (2013.01); *G06T 2207/10024* (2013.01); *G06T 2207/10068* (2013.01); *G06T 2207/30032* (2013.01)

(56) References Cited

U.S. PATENT DOCUMENTS

| | | | |
|---|---|---|---|
| 2008/0243054 A1* | 10/2008 | Mollstam | A61M 3/0216 |
| | | | 604/31 |
| 2010/0168584 A1* | 7/2010 | Fujinuma | G02B 23/2461 |
| | | | 600/473 |
| 2011/0230712 A1 | 9/2011 | Matsuura et al. | |
| 2011/0237880 A1* | 9/2011 | Hamel | A61B 1/00009 |
| | | | 600/104 |
| 2011/0275889 A1 | 11/2011 | Kase et al. | |
| 2012/0092472 A1 | 4/2012 | Higuchi | |
| 2012/0182409 A1* | 7/2012 | Moriyama | A61B 1/00006 |
| | | | 348/65 |
| 2014/0046131 A1* | 2/2014 | Morita | H04N 5/3572 |
| | | | 600/109 |
| 2014/0171738 A1* | 6/2014 | Kagaya | A61B 1/051 |
| | | | 600/109 |
| 2015/0077529 A1* | 3/2015 | Hatta | H04N 13/128 |
| | | | 348/54 |
| 2015/0080652 A1* | 3/2015 | Staples, II | G06T 7/70 |
| | | | 600/109 |
| 2016/0239967 A1* | 8/2016 | Chou | G06T 7/11 |
| 2017/0042407 A1* | 2/2017 | Miyai | H04N 5/232123 |

FOREIGN PATENT DOCUMENTS

| | | |
|---|---|---|
| JP | 2012-035696 | 10/2012 |
| JP | 2012-245157 | 12/2012 |
| WO | 2008/024419 | 2/2008 |
| WO | 2011/016428 | 2/2011 |
| WO | 2011/055614 | 5/2011 |

\* cited by examiner

IMAGE PROCESSING DEVICE, IMAGE PROCESSING METHOD, AND IMAGE PROCESSING PROGRAM FOR DETECTING SPECIFIC REGION FROM IMAGE CAPTURED BY ENDOSCOPE DESIGNATED AS DETECTION TARGET IMAGE IN RESPONSE TO DETERMINING THAT OPERATOR'S ACTION IN NOT PREDETERMINED ACTION

CROSS-REFERENCE TO RELATED APPLICATION(S)

This application is a continuation application of PCT Application No. PCT/JP2015/068736 filed Jun. 29, 2015, which is hereby incorporated by reference in its entirety.

TECHNICAL FIELD

The present invention relates to an endoscope system having an image processing device that detects an abnormal portion from an image captured by an endoscope used to make an intravital observation, and method of producing images based on an image processing program.

DESCRIPTION OF THE RELATED ART

Recently, endoscopes have become widely available as medical observation instruments capable of making noninvasive observations of lumens in living bodies. The development of diagnostic support technology is rapidly growing such that to remove certain images captured by an endoscope and are unsuitable for observation in advance and to extract images having specific characteristics such as lesions, and to improve the image quality of observation target images in advance.

For example, Japanese Patent Application which is a Japanese Translation of PCT International Application Publication No. JP-T-2010-512173 discloses a technique to delete low-quality images containing blurring, specular reflection, and the likes in which these images are unnecessary for diagnosis, and therefore to improve image quality such as contrast enhancement and super-resolution as pre-processing in making a diagnosis based on pit pattern analysis or the like.

Furthermore, the aforementioned Japanese Patent Application teaches that images unnecessary for diagnosis are determined based on the image quality and the image quality of diagnosis target images is improved to promote the efficiency of diagnostic support and resulting in limited promotion of the efficiency of diagnostic support, such as to perform processing excessively on images fundamentally unnecessary for diagnosis.

BRIEF SUMMARY OF EMBODIMENTS

Processing necessary for images captured by an endoscope can be expected to some extent depends on an action taken by an operator of the endoscope such as a doctor during image capturing. For example, when the operator conducts some kind of treatment on a subject body, such as a lesion that has already been identified, there is less need to further diagnose images captured during the treatment. Moreover, when the operator is making an observation using special light such as narrow-band light, since a lesion that being identified already is likely to be differentiated, then there is less need to make a search in a new or different form for the lesion from the images captured under the special light.

The present disclosure relates to an endoscope system capable of determining an image captured by an endoscope and in which necessity for diagnosis is low, according to an operator's action on the endoscope to achieve efficient diagnostic support. The endoscope system includes an endoscope, a light source device, an imaging processing device, and a display device all of which electronically communicate to one another to determine, differentiate, classify, and to decide whether one or more images captured by the endoscope are suitable for diagnostic purposes. The image processing device according to the present disclosure includes an action determination unit that determines, based on an image captured by an endoscope inserted into a subject body, an operator's action on the endoscope at the time of capturing the image. An image decision unit then decides whether the image is set as a detection target image for a specific region based on the determination result by the action determination unit. Finally, a detection unit detects the specific region from the detection target image.

An image processing method according to the present disclosure includes an action determination step of causing an arithmetic unit to determine, based on an image captured by an endoscope inserted into a subject body, an operator's action on the endoscope at the time of capturing the image. Next, an image decision step of causing the arithmetic unit to decide whether the image is set as a detection target image for a specific region based on the determination result in the action determination step. And finally, a detection step of causing the arithmetic unit to detect the specific region from the detection target image.

The image processing device of the present disclosure is controlled by a computer program product including a non-transitory computer readable medium having computer program code encoded thereon that when executed by a processor of a computer causes the computer to perform the operations of an action determination step of determining an operator's action on the endoscope at the time of capturing the image. Next, the image decision step is deciding whether the image is set as a detection target image for a specific region based on the determination result in the action determination step. Finally, a detection step is detecting the specific region from the detection target image.

According to the present disclosure, since a detection target image for a specific region is decided according to the operator's action on an endoscope at the time of image capturing, an image necessary for diagnosis can be extracted to detect the specific region. This can achieve efficient diagnostic support.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every Figure. The drawings are not necessarily to scale, emphasis instead being placed upon illustrating embodiments, principles, and concepts. The structural elements having the same functions are given the same reference signs throughout the drawings. Thus, features and advantages of the present disclosure will become more apparent from the following detailed description of exemplary embodiments thereof taken in conjunction with the accompanying drawings.

DETAILED DESCRIPTION OF EMBODIMENTS an endoscope system having an image processing device, an image processing method, and an image processing program according to embodiments of the present disclosure will be described below with reference to the accompanying drawings. Note that the present disclosure is not limited to these embodiments.

Figure 1:
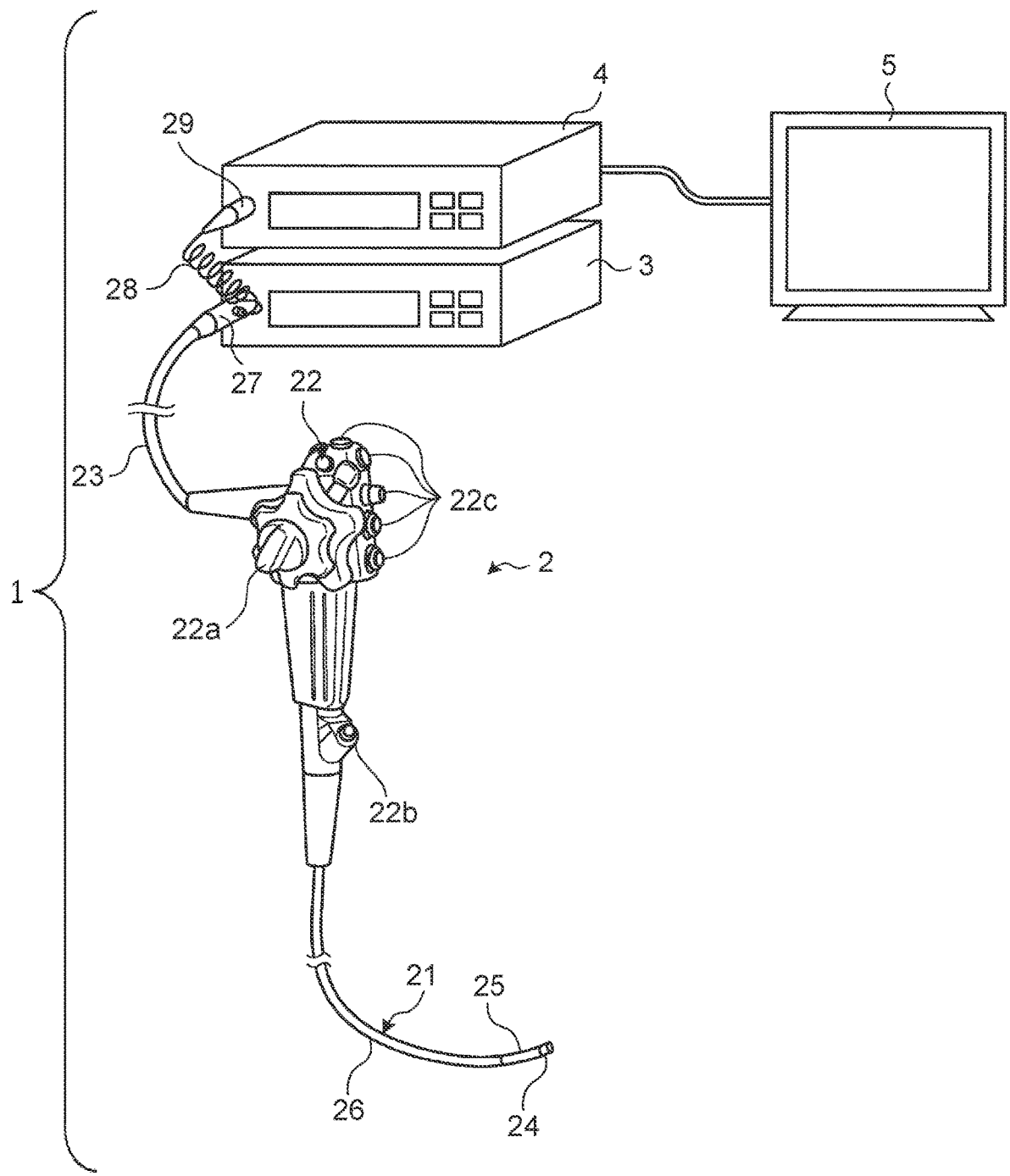
FIG. 1 is a schematic diagram illustrating the configuration of an endoscope system according to a first Embodiment of the present disclosure.

FIG. 1 is a schematic diagram illustrating a configuration example of an endoscope system according to all Embodiments of the present disclosure. An endoscope system 1 illustrated in FIG. 1 includes an endoscope 2 inserted into a subject body to capture, generate, and output images. A light source device 3 generates illumination light to be emitted from the distal end of the endoscope 2. An image processing device 4 that performs various image processing on the images generated by the endoscope 2, and a display device 5 that displays images after being subjected to the image processing by the image processing device 4.

The endoscope 2 includes a flexible, elongated insertion section 21 and a control section 22 connected to a base end side of the insertion section 21 to accept input of various manipulated signals. A universal cord 23 with various built-in cables is connected to the image processing device 4 and the light source device 3. The universal cord 23 extends in a direction different from the direction of the insertion section 21 which both extends from the control section 22. The insertion section 21 has a distal end 24, a bending section 25 composed of plural bending pieces to be freely bendable, and a long flexible needle tube 26 having flexibility and being connected to the base end side of the bending section 25. Provided at the distal end 24 of this insertion section 21 are an illumination unit that illuminates the inside of a subject body (not shown) under illumination light generated by the light source device 3. An imaging unit is defined by an optical system and an imaging device. The optical system collects illumination light reflected inside the subject body. An imaging device receives the illumination light collected by the optical system and performs photoelectric conversion to generate an image signal. By way of non-limiting example, the imaging device can be charge-coupled device (CCD) and/or complementary-metal-oxide-semiconductor (CMOS).

A cable assembly includes various signal line cables used to exchange electric signals with the image processing device 4 are bundled together, and a light guide that transmits light are connected between the control section 22 and the distal end 24. The various signal line cables include at least one signal line cable used to transmit to the image processing device 4, the image signal output from the imaging device, and a signal line cable used to transmit to the imaging device, a control signal output from the image processing device 4. As one of ordinary skill in the art would appreciate that the entire operation described hereinbefore can be done wirelessly.

The control section 22 has a bending knob 22a that bends the bending section 25 in the vertical and horizontal directions. A treatment tool inserting part 22b from which treatment tools, such as a biopsy needle, biopsy forceps, a laser knife, and an inspection probe are inserted, and plurality of switches 22c, as input units, are used to input operation instruction signals to peripheral equipment, such as an air-supply unit, a water-supply unit, and a gas-supply unit, in addition to the image processing device 4 and the light source device 3.

The universal cord 23 incorporates at least the light guide and the cable assembly. Further, on an end side different from the side of the universal cord 23 to be connected to the control section 22, a connector 27 is attached to the light source device 3. An electric connector 29 is electrically connected to the connector 27 through a coil cable 28 having a coil shape and attachable to the image processing device 4 are provided. The image signal output from the imaging device is input to the image processing device 4 through the coil cable 28 and the electric connector 29. Further, information on operations carried out to the control section 22, information on the type of illumination light output from the light source device 3 (normal light, special light, or the like) and the intensity of light, and the like are input as system information to the image processing device 4 through the coil cable 28 and the electric connector 29.

Figure 2:
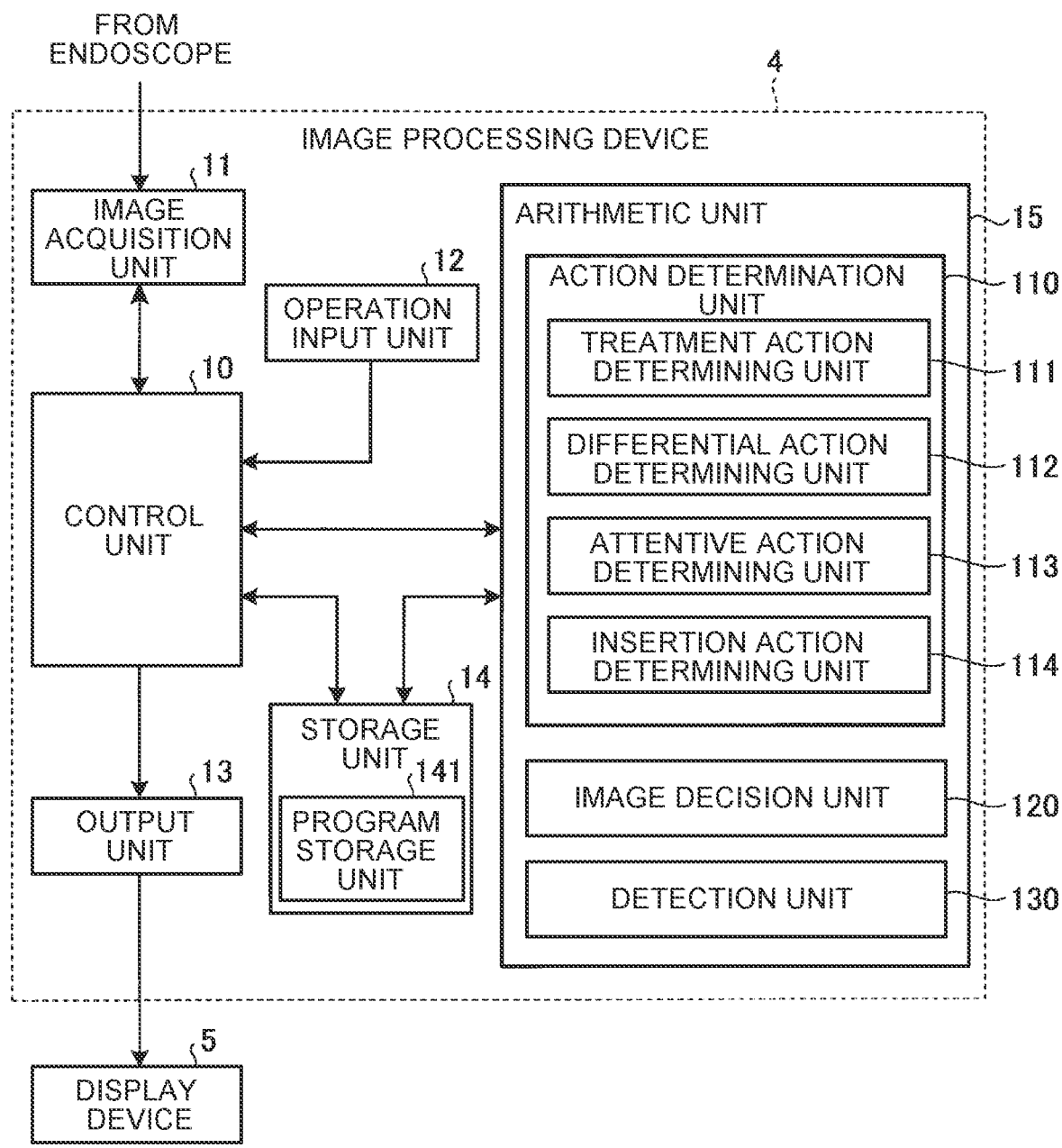
FIG. 2 is a block diagram illustrating the configuration of an image processing device illustrated in FIG. 1.

FIG. 2 is a block diagram illustrating the configuration of the image processing device 4 illustrated in FIG. 1. The image processing device 4 performs image processing on images captured during examination using the endoscope 2 in response to the actions of an operator of the endoscope during capturing the images. The images captured by the endoscope 2 are typically color images having pixel levels (pixel values) of wavelength components of R (red), G (green), and B (blue) at respective pixel positions.

As illustrated in FIG. 2, the image processing device 4 includes a control unit 10 that controls the entire operation of the image processing device 4. An image acquisition unit 11 acquires images from the endoscope. An operation input unit 12 inputs an input signal to the control unit 10 in response to an operation from the outside. An output unit 13 used as an interface to output a display image signal to the display device 5. A storage unit 14 stores the images acquired by the image acquisition unit 11 and various programs. An arithmetic unit 15 performs predetermined image processing on image data.

The control unit 10 is configured using a general-purpose processor such as a CPU (Central Processing Unit), or a special-purpose processor such as any of various arithmetic circuits executing specific functions like an ASIC (Application Specific Integrated Circuit). When the control unit 10 is the general-purpose processor, the processor reads each of various programs stored in the storage unit 14 to give instructions or transfer data to each of units constituting the image processing device 4 so as to control the entire operation of the image processing device 4. When the control unit 10 is a special-purpose processor, the processor may execute various processes alone or execute various processes using various data and the like stored in the storage unit 14 in such a manner that the processor and the storage unit 14 cooperate or are combined with each other.

The image acquisition unit 11 is implemented by an interface that takes in images from the endoscope 2. Alternatively, the image acquisition unit 11 may have such a structure that images output from the endoscope 2 are temporarily accumulated in a storage device such as a server. In this case, the image acquisition unit 11 is implemented by a communication device or the like connected to the server to perform data communication with the server in order to acquire the images.

The operation input unit 12 is implemented by input devices such as a keyboard and a mouse, a touch panel, and various switches to input to the control unit 10, input signals generated in response to operations of these input devices from the outside.

The output unit 13 outputs display image signals to the display device 5 under the control of the control unit 10 to display various screens.

The storage unit 14 is implemented by various integrated circuit (IC) memories such as flash memories capable of update recording like a ROM and a RAM. A hard disk is built in or connected through data communication terminal or an information storage medium such as a CD-ROM and an information writing/reading device for the information storage medium, and the like. The storage unit 14 stores a program for operating the image processing device 4 and causing the image processing device 4 to execute various functions and/or data used while this program is running. Moreover, the storage unit 14 stores image data acquired by the image acquisition unit 11. Specifically, the storage unit 14 has a program storage unit 141 for storing an image processing program that causes the image processing device 4 to perform image processing on images captured by the endoscope according to the operator's actions during image capturing.

The arithmetic unit 15 is configured using a general-purpose processor such as a CPU, or a special-purpose processor such as any of various arithmetic circuits executing specific functions like an ASIC. When the arithmetic unit 15 is the general-purpose processor, the arithmetic unit 15 reads the image processing program stored in the program storage unit 141 to perform image processing on images captured by the endoscope according to the operator's actions during image capturing. When the arithmetic unit 15 is a special-purpose processor, the processor may execute various processes alone or execute various processes using various data and the like stored in the storage unit 14 in such a manner that the processor and the storage unit 14 cooperate or are combined with each other to perform image processing.

Next, the configuration of the arithmetic unit 15 will be described. As illustrated in FIG. 2, the arithmetic unit 15 includes an action determination unit 110 that determines, based on an image in a subject body captured by the endoscope 2, an operator's action at the time of capturing the image. Next, an image decision unit 120 decides whether the image is set as a detection target image for an abnormal region according to the determination result of the operator's action. Finally, a detection unit 130 that detects the abnormal region from the detection processing target image. As a non-limiting example, the abnormal region is defined as a specific region like a lesion exhibiting an aspect different from those of normal mucosal regions, which is identified by color feature value, shape feature value, texture feature value, or the like, depending on the type of abnormality.

The action determination unit 110 includes a treatment action determining unit 111, a differential action determining unit 112, an attentive action determining unit 113, and an insertion action determining unit 114. The action determination unit 110 may include at least one of these determination units, or include all of these four determination units.

The treatment action determining unit 111 determines whether the operator's actions at the time of capturing determination target images are treatment actions that give a subject body medical treatments. Without being limiting, the treatment actions include an action to give a medical treatment using various treatment tools such as an action to supply water into the subject body to wash out.

Figure 3:
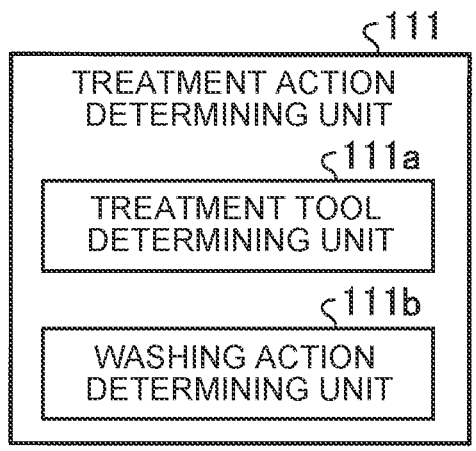
FIG. 3 is a block diagram illustrating the configuration of a treatment action determining unit illustrated in FIG. 2.

FIG. 3 is a block diagram illustrating the configuration of the treatment action determining unit 111. As illustrated in FIG. 3, the treatment action determining unit 111 has a treatment tool determining unit 111*a* and a washing action determining unit 111*b*. The treatment action determining unit 111 may have at least either or both of the treatment tool determining unit 111*a* and the washing action determining unit 111*b* during the operation. The treatment action determining unit 111 determines the presence or absence of a treatment action based on the determination results of these determination units.

The treatment tool determining unit 111*a* determines whether a treatment tool region, in which a treatment tool used to treat the subject body comes out, is detected from an image. Examples of treatment tools used in endoscopy include a high-frequency snare used in polypectomy to remove a polyp as a lesion locally raised from the mucosal epithelium, hot biopsy forceps used in hot biopsy to nip and cut a tiny polyp with no constriction, an injection needle to inject normal saline into a submucosal layer in removing a lesion such as an early stage cancer which is flat with few bumps, and the like.

All of these treatment tools have metal tips and are each provided at the distal end of a tube-shaped shaft. Therefore, when illumination light is emitted by the endoscope, the emitted light appears in an image as a high-brightness tube-shaped region. The treatment tool determining unit 111*a* detects, as a treatment tool region, a tube-shaped region whose brightness is higher than a threshold value. Specifically, the treatment tool determining unit 111*a* first creates a brightness histogram from RGB (Red, Green, Blue) color components of each pixel in the image, decides on a threshold value based on a major distribution peak of a mucosal region or the like to perform threshold value processing so as to extract a high-brightness region. Then, the contour of this high-brightness region is extracted to determine, by Hough transform or the like, whether this contour has a geometric shape composed of straight lines and circular forms. When the contour of the high-brightness region has a geometric shape, this high-brightness region is determined to be a treatment tool region. When a treatment tool region is detected from the image, the treatment tool determining unit 111I determines that a treatment action using the treatment tool was taken at the time of image capturing.

The washing action determining unit 111b determines whether a washed region, in which washing water supplied to the subject body comes out, is detected from the image. The washed region bears specular reflection caused by reflecting the illumination light on the water surface or water drops, and the area and position of the washed region widely vary with time. Therefore, the washing action determining unit 111b detects, as the washed region, a region the brightness of which is high and the area and position of which widely vary with time. In detail, the washing action determining unit 111b first calculates brightness from the pixel value of each pixel in the image, and performs threshold value processing on the brightness to extract a high-brightness region. Then, based on the brightness near the boundary of the extracted high-brightness region, a high-brightness region with a great difference in brightness near the boundary is extracted as a specular reflection region. Further, differences in the area and position of the specular reflection region between the image and an image preceding by a predetermined number of frames (e.g., the previous frame) are acquired, and when these differences are larger than threshold values, the specular reflection region is determined to be a washed region.

Alternatively, the washing action determining unit 111b may detect, as the washed region, a region with a specific frequency component (e.g., high-frequency component) widely varying with time in the image. When the washed region is detected from the image, the washing action determining unit 111b determines that a washing action was taken at the time of image capturing.

As another method of determining a treatment action, a sensor may be provided in the treatment tool inserting part 22b of the endoscope 2 to detect that a treatment tool is inserted in the subject body to acquire, from the endoscope 2, a detection signal output from this sensor in order to systematically determine whether a treatment action is taken. Alternatively, a signal indicating that a pump to supply water from a water supply tank to the endoscope 2 is in operation may be acquired from the endoscope system 1 to systematically determine that the washing action is taken.

The differential action determining unit 112 determines whether an operator's action during capturing a determination target image is a differential action to determine (diagnose) the degree of a lesion observed in an image.

Figure 4:
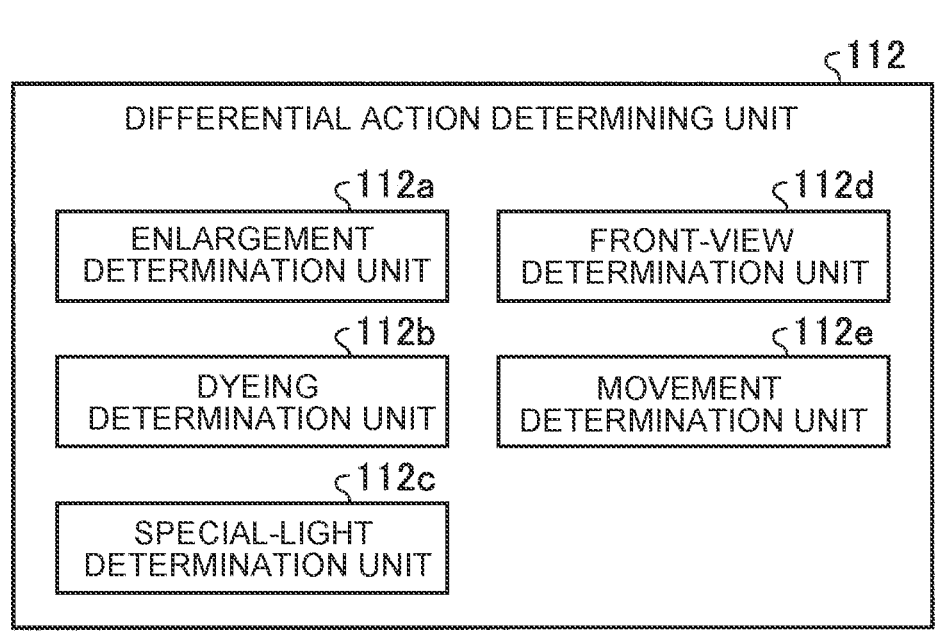
FIG. 4 is a block diagram illustrating the configuration of a differential action determining unit illustrated in FIG. 2.

FIG. 4 is a block diagram illustrating the configuration of the differential action determining unit 112. As illustrated in FIG. 4, the differential action determining unit 112 has an enlargement determination unit 112a, a dyeing determination unit 112b, a special-light determination unit 112c, a front-view determination unit 112d, and a movement determination unit 112e. The differential action determining unit 112 may have at least one of these determination units, or may have all of the determination units. The differential action determining unit 112 determines the presence or absence of a differential action based on the determination results of these determination units.

The enlargement determination unit 112a determines whether a determination target image is an enlarged image, i.e., whether the determination target image is an image captured in such a manner that the distal end 24 of the endoscope 2 is brought close to the mucous membrane at a predetermined distance or less. In detail, the enlargement determination unit 112a first acquires distance information near the center of the image. Here, the distance information is information representing distance from the distal end 24 of the endoscope 2 to a subject. As the distance information, a value with less absorption by blood vessels and the like that appear in a mucosal surface as the subject, and correlated with the distance to the mucosal surface is used.

For example, since a wavelength component corresponding to R component among pixel values of RGB color components is far away from a hemoglobin absorption band, and hardly affected by absorption and scattering in the living body due to a long wavelength, the attenuation of this wavelength component corresponds to the distance traveling in the subject body. Therefore, the R component value can be used as the distance information. In this case, it can be determined that the distance is closer as the R component value is larger, and that the distance is farther as the R component value is smaller. Based on such distance information, the enlargement determination unit 112a determines an image, in which distance near the center of the image is smaller than a threshold value, to be an enlarged image. For example, when the R component value is used as the distance information, an image, in which the R component pixel value of each pixel near the center of the image is larger than the threshold value, is determined to be the enlarged image.

As another method of determining an enlarged image, the enlargement determination unit 112a may analyze a pit pattern in the image. When the operator enlarges an image, the image is often an image in which a pit pattern on the mucous membrane is to be observed in detail. Therefore, the operator manipulates the endoscope 2 to cause the pit pattern to come out clearly as an enlarged image to some extent. In this case, a frequency component to be extracted from the pit pattern in enlarging the image can be acquired in advance to compare this frequency component with a frequency component extracted from the determination target image so as to determine whether the determination target image is an enlarged image.

As still another method of determining the enlarged image, the enlargement determination unit 112a may acquire, from the endoscope 2, a switching signal when an image capturing mode of the endoscope 2 is switched to magnification observation to make a systematic determination.

The dyeing determination unit 112b determines whether the determination target image is a dyed image in which the mucous membrane as the subject is dyed. In detail, the dyeing determination unit 112b first sets a target region in the image, and calculates an average color from the RGB color components of each pixel in this target region. Then, it is determined whether this average color is deviated from a hue distribution of normal mucosal regions. For example, when the mucous membrane is dyed with indigocarmine used in colorectal examination, the average color is deviated to blue. In such a case, the dyeing determination unit 112b determines that the image is a dyed image.

The special-light determination unit 112c determines whether the determination target image is a special-light image captured using special light. In detail, the special-light determination unit 112c first sets a target region in the image, and calculates an average color from the RGB color components of each pixel in this target region. Then, it is determined whether this average color is deviated from a hue distribution of normal mucosal regions. For example, when the image is captured using narrow-band light in a wavelength band of green in which blood vessels deep in the mucous membrane come out, the average color is deviated to green. In such a case, the special-light determination unit 112c determines that the image is a special-light image.

As another method of determining the special-light image, the special-light determination unit 112c may acquire, from the endoscope 2, a switching signal when an image capturing mode of the endoscope 2 is switched to a special-light image capturing mode to make a systematic determination.

The front-view determination unit 112d determines whether the determination target image is a front-view image in which the mucous membrane as the subject is captured from the front view. The front view means a state where the imaging unit provided at the distal end 24 of the endoscope 2 has such a visual field as to capture, from the front view, the mucous membrane located on the side of a lumen.

Here, illumination light is hard to reach a ductal deep portion located in the depth direction of the lumen. Therefore, when the visual field of the imaging unit faces the direction of the ductal deep portion, a low-brightness ductal deep region comes out near the center in the image. Further, in this case, since the mucous membrane located on the side of the lumen appears obliquely, the gradient strength of a mucosal region in the image becomes large. On the other hand, when the visual field of the imaging unit faces the direction of the mucous membrane, the ductal deep region disappears from the image to cause the mucosal region to be dominant and the gradient strength of the mucosal region to become small. Therefore, the front-view determination unit 112d determines, as a front-view image, an image from which no ductal deep region is detected and in which the mucosal region is dominant, i.e., the mucosal region occupies a predetermined proportion of the area in the image and the gradient strength of the mucosal region is less than or equal to a threshold value. The gradient strength of the mucosal region can be calculated based on distance information in the mucosal region.

The ductal deep region is detected as a region with low brightness, having a certain size of area, and having a shape relatively similar to a circular form (not an elongated shape). Therefore, the front-view determination unit 112d first detects, from the image, a low-brightness region whose brightness is less than or equal to the threshold value, and determines whether the area of this low-brightness region is more than or equal to a predetermined value. When the area of the low-brightness region is more than or equal to the predetermined value, the front-view determination unit 112d further determines whether the low-brightness region has an elongated shape. The determination of the elongated shape can be made, for example, in such a manner that the proportion of the area of the low-brightness region to the area of a rectangle circumscribed about the low-brightness region is calculated to determine the elongated shape based on this proportion. Specifically, when this proportion is less than or equal to a predetermined value, the shape of the low-brightness region is an elongated shape, and the low-brightness region is determined not to be the ductal deep region. On the other hand, when the above proportion is more than the predetermined value, the low-brightness region is a shape relatively similar to a circular form (not an elongated shape), and the low-brightness region is determined to be the ductal deep region.

The movement determination unit 112e determines whether an image of a structure with less movement appearing in the image is captured continuously during a predetermined period or more. In detail, the movement determination unit 112e first calculates an amount representing the movement of the structure corresponding to that of an image preceding by a predetermined number of frames (e.g., one frame or a few frames) to extract, as the image with less movement, an image with this amount being less than or equal to a threshold value. Then, the movement determination unit 112e determines whether the determination target image is an image with less movement and the image with less movement is captured continuously during the predetermined period or more prior to the determination target image.

An example of the amount representing the movement of the structure appearing in the image will be described. First, the image is divided into plural rectangular regions to calculate a motion vector for each rectangular region by a block matching method. As of ordinary skill in the art would appreciate the general theory of block matching method is well known in the art and will not discussed hereinafter. Then, a representative value (such as the maximum value or the average value) for the length of a motion vector representing the amount of movement of rectangular regions high in correlation value between images to be compared can be used as an amount representing the movement of the structure.

The attentive action determining unit 113 determines whether an operator's action at the time of capturing the determination target image is an attentive action of the operator to pay close attention to a certain region in the subject body.

Figure 5:
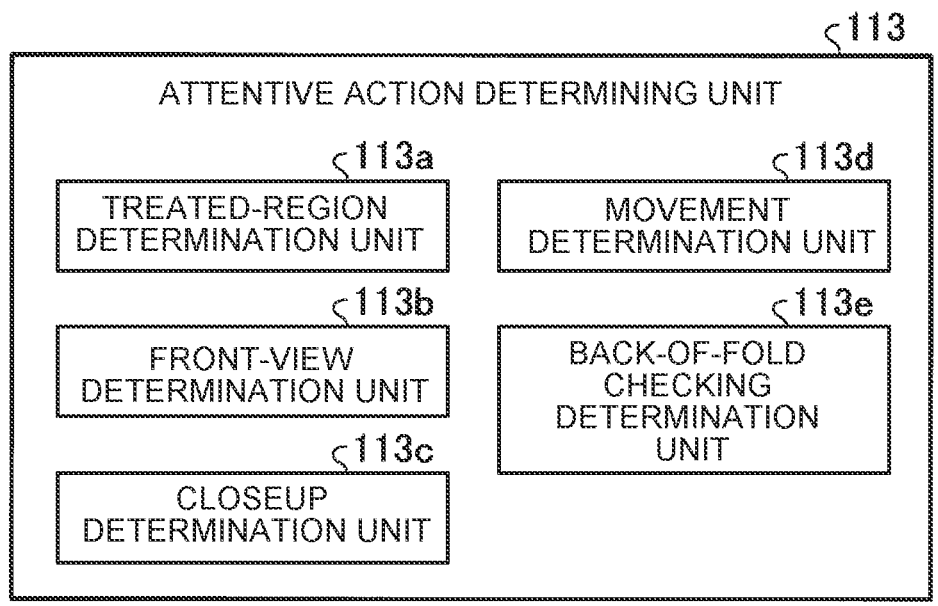
FIG. 5 is a block diagram illustrating the configuration of an attentive action determining unit illustrated in FIG. 2.

FIG. 5 is a block diagram illustrating the configuration of the attentive action determining unit 113. As illustrated in FIG. 5, the attentive action determining unit 113 has a treated-region determination unit 113a, a front-view determination unit 113b, a close-up determination unit 113c, a movement determination unit 113d, and a back-of-fold checking determination unit 113e. The attentive action determining unit 113 may have at least one of these units, or have all of the units. The attentive action determining unit 113 determines the presence or absence of an attentive action based on the determination results of these determination units.

The treated-region determination unit 113a determines whether there is a region in which the determination target image underwent a treatment a short time ago. When there is a region in which the determination target image underwent a treatment a short time ago, it is considered that the operator paid close attention to the treated region. When a treatment is given in the subject body, a region with a tool such as a hemostatic clip and the stigmata of bleeding are observed. The treated-region determination unit 113a detects such a region with a tool and the stigmata of bleeding as a treated region for which the treatment was given a short time ago.

The tool such as a clip is observed as a tube-shaped region different in color from the mucosal region in the image. Therefore, the treated-region determination unit 113a first calculates a distribution of color feature values from RGB color components of each pixel in the image, and extracts, as a candidate region, a region exhibiting a distribution different from a distribution of color feature values for the mucosal region. Then, the treated-region determination unit 113 a extracts a contour from the candidate region, and further performs processing by Hough transform or the like to extract a geometric shape of straight lines and curved lines from this contour. Then, the treated-region determination unit 113a determines a candidate region with the geometric shape extracted from the contour as a region in which the tool comes out. As for a bleeding region, a color ratio G/R is calculated from RGB color components of each pixel in the image, and threshold value processing is performed on this color ratio to extract a bright red-color region.

The front-view determination unit 113b determines whether the determination target image is a front-view image in which the mucous membrane is captured from the front view. The method of determining the front-view image is the same as that of the front-view determination unit 112d in the differential action determining unit 112 and will not describe again to avoid redundancy.

The close-up determination unit 113c determines whether the determination target image is a close-up image in which a region whose distance from the distal end 24 of the endoscope 2 is less than or equal to a predetermined value is captured. In detail, the close-up determination unit 113c first acquires distance information in each part of the image, and calculates a representative value (such as the maximum value or the average value) of each of these pieces of distance information. Then, when this representative value falls within a predetermined range, the image is determined to be a close-up image. The R component value of each pixel value can be used as the distance information like in the determination of an enlarged image as mentioned above.

The movement determination unit 113d determines whether an image of a structure with less movement appearing in the image is captured continuously during a predetermined period or more. The calculation method and determination method for an amount representing the movement of the structure are the same as those of the movement determination unit 112e in the differential action determining unit 112.

The back-of-fold checking determination unit 113e determines whether the determination target image is an image captured during the action to check the back of a fold of the mucous membrane. This determination is made by determining whether part of the insertion section 21 of the endoscope 2 appears in the image.

Figure 6:
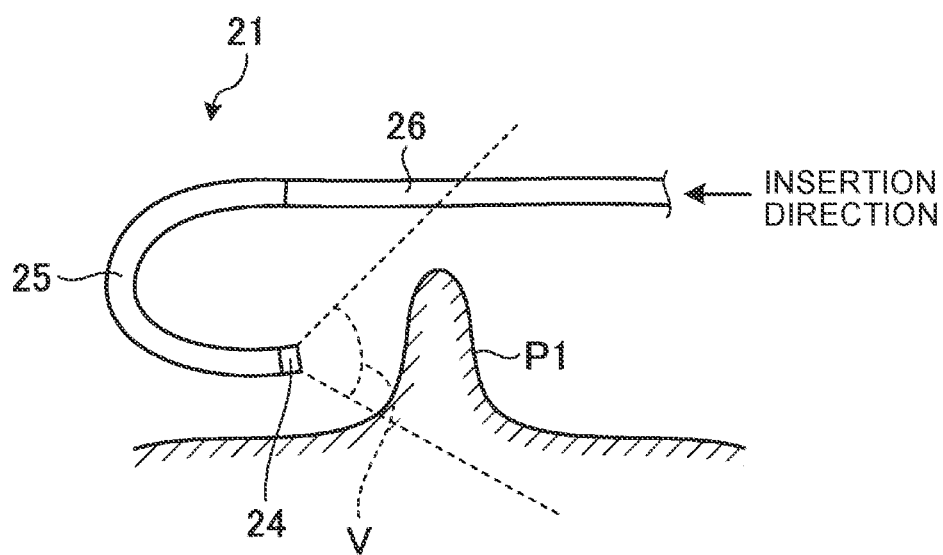
FIG. 6 is a schematic diagram for describing a back-of-fold checking action.

FIG. 6 is a schematic diagram for describing the back-of-fold checking action. As illustrated in FIG. 6, when the back side of a fold P1 of the mucous membrane in the insertion direction of the insertion section 21 of the endoscope 2 (see FIG. 1) is to be observed, the bending section 25 is so bent that the base end side will turn around. In this case, the insertion section 21 itself may come out in a visual field V of the imaging unit provided at the distal end 24. When part of the endoscope 2 comes out in an image like in the above case, the back-of-fold checking determination unit 113e determines that the image was captured during the back-of-fold checking action.

The region in which the insertion section 21 of the endoscope 2 comes out is detected as a tube-shaped region that exhibits a distribution different from a distribution of color feature values of a mucosal region. Specifically, the insertion section 21 exhibits a color distribution near black color. Therefore, based on the RGB color components of each pixel in the image, the back-of-fold checking determination unit 113e first extracts, as a candidate region, a region included in a distribution of color feature values possibly taken by the insertion section 21. Then, the back-of-fold checking determination unit 113e extracts a contour from the candidate region to extract a geometric shape of straight lines and curved lines from this contour by Hough transform or the like. Then, when the geometric shape is extracted from the contour, the candidate region is determined to be part of the insertion section 21.

The insertion action determining unit 114 determines whether the operator's action at the time of capturing the determination target image is an insertion action to insert the endoscope in a direction from the anus toward the appendix of the subject body. Here, when the large intestine is to be examined using the endoscope, the endoscope is usually inserted into the large intestine from the anus, and after the distal end 24 of the endoscope 2 is moved forward near the appendix, a lesion portion or the like is observed in a return path to pull out the endoscope 2 from the large intestine. Thus, the operator pays close attention to the insertion action in a forward path to insert the endoscope 2 and does not often make an observation as a diagnosis. Therefore, the determination of whether the operator's action is the insertion action (forward path) or the removal action (return path) of the endoscope 2 is related to an issue of the selection of a diagnosis target image.

Figure 7:
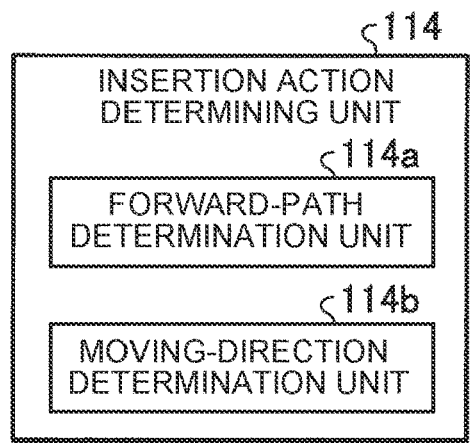
FIG. 7 is a block diagram illustrating the configuration of an insertion action determining unit illustrated in FIG. 2.

FIG. 7 is a block diagram illustrating the configuration of the insertion action determining unit 114. As illustrated in FIG. 7, the insertion action determining unit 114 includes a forward-path determination unit 114a and a moving-direction determination unit 114b. The insertion action determining unit 114 may have at least either of the forward-path determination unit 114a and the moving-direction determination unit 114b, or both. The insertion action determining unit 114 determines the presence or absence of the insertion action based on the determination results of these determination units.

The forward-path determination unit 114a determines whether the endoscope 2 (see FIG. 1) inserted in the subject body is moving in the forward path, i.e., in a direction from the anus toward the side of the small intestine. In detail, based on at least either of an insertion length, as the length of an inserted part of the insertion section 21 (see FIG. 6) of the endoscope 2 inserted in the large intestine, and an insertion shape of the insertion section 21 to be bent along the shape of the large intestine, the forward-path determination unit 114a determines whether the endoscope 2 is moving in the forward path. An endoscope insertion shape observation device (UPD) can be provided in the endoscope 2 to acquire the insertion length and the insertion shape as system information. Based on the insertion length or the insertion shape obtained from the UPD, the forward-path determination unit 114a determines, as the forward path, a section until the distal end 24 of the endoscope 2 reaches the vicinity of the appendix.

Alternatively, the forward-path determination unit 114a may determine whether the neighborhood of the appendix comes out in images captured sequentially by the endoscope 2 to determine, as the forward path, a section until the appearance of an image in which the neighborhood of the appendix first comes out.

Here, when the appendix is observed from the side of the large intestine, since the appendix is a dead-end tube except for being connected to the small intestine through the ileocecal valve, a ductal deep region does not come out in the image. Therefore, when the ductal deep region disappears from an image despite the progress of the endoscope 2 along the tube shape of the large intestine, it can be determined that the distal end 24 of the endoscope 2 reaches the neighborhood of the appendix. The method of detecting the ductal deep region is the same as that of the front-view determination unit 112d (see FIG. 4) in the differential action determining unit 112 and will not describe again to avoid redundancy.

However, when the distal end 24 views the mucous membrane from the front, the ductal deep region will disappear from an image even if the distal end 24 does not reach the neighborhood of the appendix. Therefore, when a mucosal region is dominant in the image, it may be determined whether the distal end 24 reaches the neighborhood of the appendix based on the brightness gradient strength of the mucosal region. When the brightness gradient strength of the mucosal region is small (less than or equal to a threshold value), the distal end 24 is determined to view the mucous membrane from the front. Therefore, if the distal end 24 turns around, the ductal deep region will have the potential to appear. On the other hand, when the brightness gradient strength of the mucosal region is large (more than the threshold value), the distal end 24 is determined to face a ductal deep direction (in the direction of forward movement). In such a state, if the ductal deep region goes out of being detected, it can be determined that the distal end 24 reaches the neighborhood of the appendix.

The moving-direction determination unit 114b determines whether the endoscope 2 is moving toward the distal end 24 of the endoscope 2 or toward the base end of the endoscope 2. When the endoscope 2 is moving toward the distal end 24 of the endoscope 2, it can be said that the endoscope 2 is moving in the forward path. On the other hand, when the endoscope 2 is moving toward the base end of the endoscope 2, it can be said that the endoscope 2 is moving in the return path.

The moving-direction determination unit 114b acquires the insertion shape of the insertion section 21, and decides on the direction of a ductal deep portion in the image based on this insertion shape. Like in the forward-path determination unit 114a, the insertion shape can be acquired as system information. For example, data on the tip position and the insertion length of the endoscope can be acquired using the endoscope insertion shape observation device. Therefore, when the insertion length becomes larger, the endoscope 2 is determined to be moving toward the distal end 24, while when the insertion length becomes shorter, the endoscope 2 is determined to be moving toward the base end. Alternatively, the direction of the ductal deep portion in the image may be detected based on the contour edge shape of a mucosal fold. Here, the contour edge of the mucosal fold is basically raised to a side opposite to the direction of the ductal deep portion. Therefore, the contour edge of the mucosal fold can be extracted to determine the indented pattern of this contour edge in order to decide on the direction of the ductal deep portion.

The moving-direction determination unit 114b further acquires a motion vector between the determination target image and an image preceding by a predetermined number of frames (e.g., the previous frame), and detects the moving direction of the endoscope 2 from a relation between this motion vector and the direction of the ductal deep portion in the image. In other words, when the direction of the motion vector is identical to the depth direction in the image, it can be said that the endoscope 2 is moving toward the distal end 24. On the other hand, when the direction of the motion vector is opposite to the direction of the ductal deep portion in the image, it can be said that the endoscope 2 is moving toward the base end.

According to the determination results by the action determination unit 110, the image decision unit 120 decides on a detection target image for an abnormal region. Specifically, images captured during any action determined by the action determination unit 110 are excluded from candidates for each detection target image for an abnormal region, and each of the other images is decided to be the detection target image for the abnormal region.

The detection unit 130 performs processing for detecting an abnormal region from the image decided by the image decision unit 120 to be the detection target image.

Figure 8:
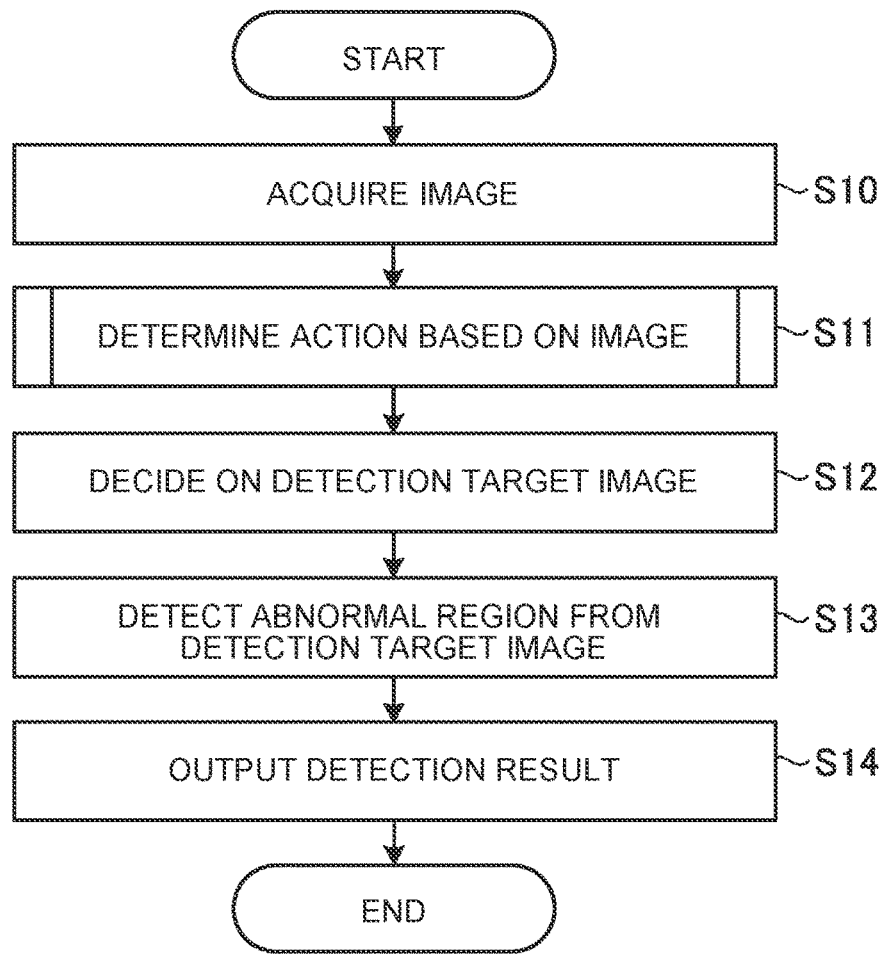
FIG. 8 is a flowchart illustrating an image processing method according to the first Embodiment of the present disclosure.

Next, an image processing method according to the first Embodiment of the present disclosure will be described. FIG. 8 is a flowchart illustrating the image processing method according to the first Embodiment.

First, in step S10, the arithmetic unit 15 acquires, as a determination target image, an image captured by the endoscope 2. In detail, when the operator enters an instruction to start an examination of a subject body in the endoscope system 1 with an operation to the operation input unit 12, the operation input unit 12 generates an input signal representing this instruction and inputs the input signal to the control unit 10. In response, the image acquisition unit 11 starts image acquisition from the endoscope 2 under the control of the control unit 10. Images acquired by the image acquisition unit 11 are once stored in the storage unit 14, and the arithmetic unit 15 reads images from the storage unit 14 in chronological order to acquire the images.

In the following step S11, the action determination unit 110 determines actions taken at the time of capturing images based on the acquired images. As mentioned above, although the action determination unit 110 has only to have at least one of the treatment action determining unit 111, the differential action determining unit 112, the attentive action determining unit 113, and the insertion action determining unit 114, the description will be made on the assumption that the action determination unit 110 has all of the units in the first Embodiment.

Figure 9:
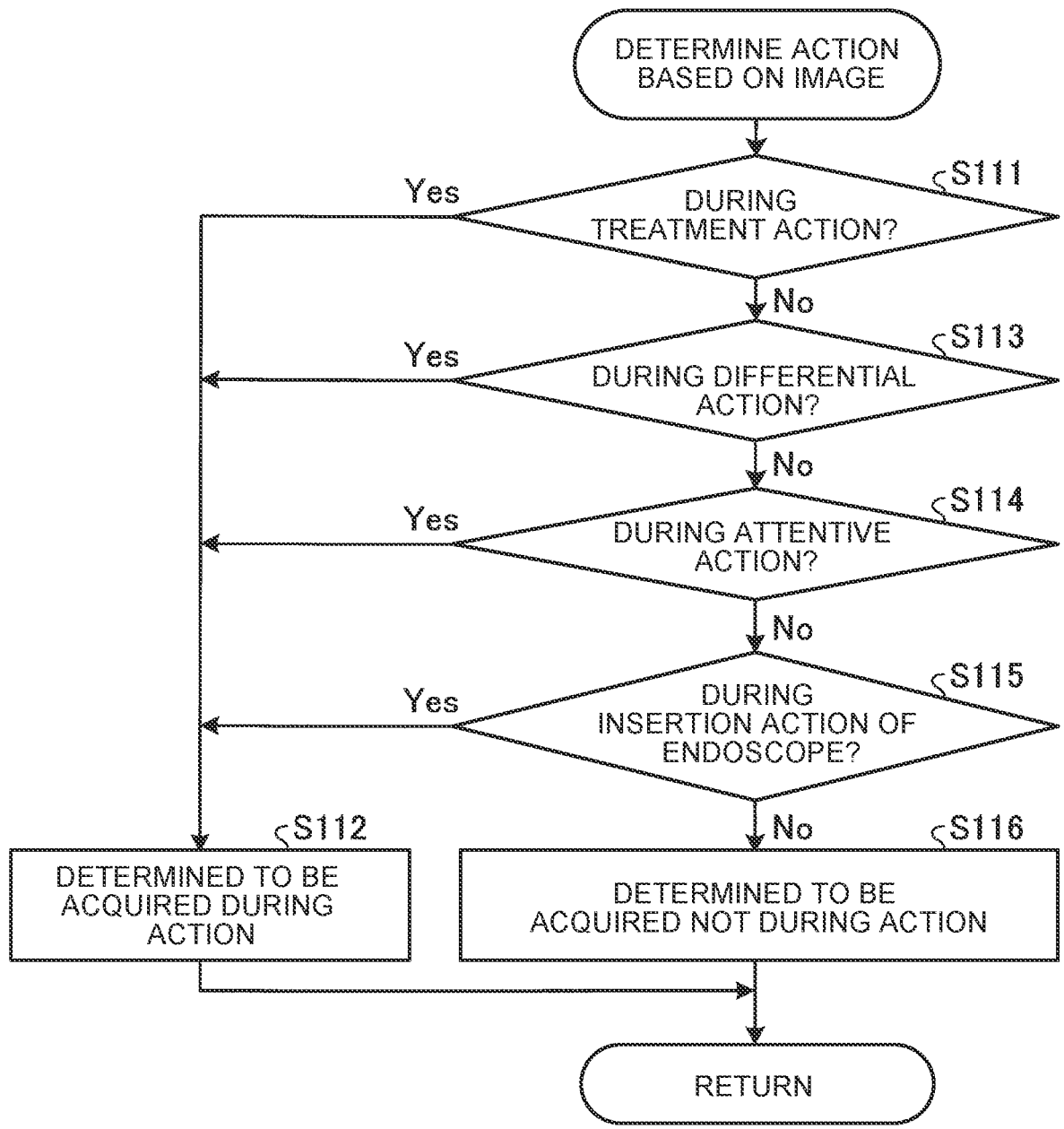
FIG. 9 is a flowchart illustrating the details of processing for determining an action based on an image.

FIG. 9 is a flowchart illustrating the details of processing for determining an action based on an image. First, in step S111, the treatment action determining unit 111 determines whether a treatment action was taken at the time of capturing the image. In the first Embodiment, it is assumed that the treatment action determining unit 111 has both the treatment tool determining unit 111a and the washing action determining unit 111b, and both units make determinations on the image, respectively. When the treatment tool determining unit 111a detects a treatment tool region from the image, or when the washing action determining unit 111b detects a washed region from the image, the treatment action determining unit 111 determines that a treatment action was taken at the time of capturing the image.

When it is determined that the treatment action was taken at the time of capturing the image (Yes command in step S111), the action determination unit 110 determines that the image was captured during the action (step S112). After that, the processing returns to the main routine. On the other hand, when it is determined that no treatment action was taken at the time of capturing the image (No command in step S111), the processing proceeds to step S113.

In step S113, the differential action determining unit 112 determines whether a differential action was taken at the time of capturing the image. In the first Embodiment, it is assumed that the differential action determining unit 112 has all of the enlargement determination unit 112a to the movement determination unit 112e, and respective units make determinations on the image, respectively. When the enlargement determination unit 112a determines that the image is an enlarged image, when the dyeing determination unit 112b determines that the image is a dyed image, when the special-light determination unit 112c determines that the image is a special-light image, when the front-view determination unit 112d determines that the image is a front-view image, or when the movement determination unit 112e determines that an image with less movement is captured continuously during a certain fixed period or more prior to the image, the differential action determining unit 112 determines that a differential action was taken at the time of capturing the image.

When it is determined that the differential action was taken at the time of capturing the image (Yes command in step S113), the processing proceeds to step S112. On the other hand, when it is determined that no differential action was taken at the time of capturing the image (No command in step S113), the processing proceeds to step S114.

In step S114, the attentive action determining unit 113 determines whether an attentive action was taken at the time of capturing the image. In the first Embodiment, it is assumed that the attentive action determining unit 113 has all of the treated-region determination unit 113a to the back-of-fold checking determination unit 113e, and respective units make determinations on the image, respectively. When the treated-region determination unit 113 a detects a treated region from the image, when the front-view determination unit 113b determines that the image is a front-view image, when the close-up determination unit 113c determines that the image is a close-up image, when the movement determination unit 113d determines that an image with less movement is captured continuously during a certain fixed period or more prior to the image, or when the back-of-fold checking determination unit 113e determines that the image was captured during a back-of-fold checking action, the attentive action determining unit 113 determines that an attentive action was taken at the time of capturing the image.

When it is determined that the attentive action was taken at the time of capturing the image (Yes in step S114), the processing proceeds to step S112. On the other hand, when it is determined that no attentive action was taken at the time of capturing the image (No in step S114), the processing proceeds to step S115.

In step S115, the insertion action determining unit 114 determines whether an endoscope insertion action was taken at the time of capturing the image. In the first Embodiment, it is assumed that the insertion action determining unit 114 has both the forward-path determination unit 114a and the moving-direction determination unit 114b, and both units make determinations on the image, respectively. When the forward-path determination unit 114a determines that the endoscope 2 is moving in the forward path, or when the moving-direction determination unit 114b determines that the endoscope 2 is moving in the direction of a ductal deep portion, the insertion action determining unit 114 determines that the endoscope insertion action was taken at the time of capturing the image.

When it is determined that the insertion action was taken at the time of capturing the image (Yes command in step S115), the processing proceeds to step S112. On the other hand, when it is determined that no insertion action was taken at the time of capturing the image (No command in step S115), the action determination unit 110 determines that the image was captured when the operator did not take any predetermined action (step S116). After that, the processing returns to the main routine.

Note that all or some of steps S111, S113, S114, and S115 mentioned above may be executed simultaneously in parallel in such a manner that the order of determination priority to plural determination results obtained in these steps will be predetermined. For example, the order of priority may be set to the treatment action determination, the differential action determination, the attentive action determination, and the insertion action determination in this order to make inquiries into the determination results in descending order of priority. Alternatively, inquiries into these determination results may be made simultaneously to determine that the image was captured during any action when it is determined that at least one action was being taken.

In step S12 following step S11, the image decision unit 120 decides, to be a detection target image for an abnormal region, an image determined to be captured when the operator did not take any predetermined action. Specifically, an image captured when all of the treatment action, the differential action, the attentive action, and the insertion action were not taken is decided to be the detection target image.

In the following step S13, the detection unit 130 detects the abnormal region from the detection target image. In detail, a mucosal region is first set as a detection target region in the detection target image. Specifically, residue regions, bubble regions, dark-part regions, and specular-reflection regions as non-mucosal regions are removed based the color feature values, the shape feature values, and the frequency components in the detection target image.

Various known methods can be used as detection methods for the residue regions, the bubble regions, the dark-part regions, and the specular-reflection regions. As an example, based on the color feature values calculated from pixel values (respective RGB color components) of each pixel in the image, a residue region can be detected as a region relatively distributed to more yellow-green side than a distributional range of color feature values of the mucous membrane. The distributional range of color feature values of the mucous membrane is acquired in advance based on the average color or the distributional range of a major color feature value in the image. Further, a bubble region can be detected as a region having a predetermined range of frequency components. A dark-part region can be detected by calculating brightness from respective RGB components of each pixel in the image and performing threshold value processing on this brightness. A specular-reflection region can be detected by extracting a white-color region based on the color feature values calculated from respective RGB color components of each pixel and interpolating boundaries by surface approximation or the like based on a change in pixel value of each of the pixels (mucosal region) surrounding this white-color region. As the color feature values, color difference calculated by converting respective RGB color components to YCbCr, hue calculated by HIS conversion, chroma saturation, and a color ratio such as G/R or B/G can be used. Alternatively, the respective RGB color components may be used intact as the color feature values.

Subsequently, the detection unit 130 sets any one or more regions in the detection target region as discriminant regions to calculate feature values for each of the discriminant regions. Various feature values, such as the color feature value, the shape feature value like a contour (edge) or a surface shape (pixel value gradient), and the texture feature value, can be used as the feature values. Then, these feature values are integrated as one feature vector to calculate a discriminant index to discriminate, based on this feature vector, whether each discriminant region is an abnormal region. A known technique can be used as the method of calculating the discriminant index. As an example, a discriminant index P(x) based on a probabilistic model as expressed in Equation (1) below is calculated. The detection unit 130 detects, as an abnormal region, a discriminant region for which the discriminant index P(x) is larger than a threshold value acquired in advance.

$$P(x) = \frac{1}{(2\pi)^{k/2} \times |Z|^{1/2}} \exp\left\{(x-\mu)^t \times \left(-\frac{1}{2}\right) Z^{-1} \times (x-\mu)\right\} \quad (1)$$

A determinant index P(x) is an index indicating whether the feature vector of a discriminant region seems to be the feature vector of an abnormal region. As the value of the determinant index P(x) becomes larger, it can be said that the discriminant region seems more likely to be the abnormal region. In other words, the determinant index P(x) expresses the degree of coincidence between the discriminant region and the abnormal region. A symbol x in Equation (1) expresses a feature vector (k rows and one column) of the determination region. Further, a symbol $\mu$ is a mean vector (k rows and one column) of feature vectors in plural abnormal-region samples acquired in advance. A symbol Z is a variance-covariance matrix (k rows and k columns) of feature vectors in plural abnormal-region samples acquired in advance. A symbol |Z| is a determinant of this matrix Z, and a symbol $Z^{-1}$ is an inverse matrix of the matrix Z.

Various methods other than the method using Equation (1) can be used to discriminate whether each discriminant region is an abnormal region. For example, the methods include a method based on the feature space distance between the feature vector of the discriminant region and a representative feature vector of the abnormal region, and a method of setting a classification boundary in the feature space.

In the following step S14, the arithmetic unit 15 outputs the detection result of an abnormal region by the detection unit 130. In detail, when the abnormal region is detected from the determination target image, the control unit 10 generates an image that highlights the detected abnormal region and displays the image on the display device 5. As an example of highlighting, a line surrounding the abnormal region or an arrow pointing to the abnormal region is superimposed on the original determination target image. Alternatively, text saying "there is an abnormal region" or the like may be superimposed on the original determination target image. After that, the processing for the determination target image is ended.

As described above, according to the first Embodiment, since an operator's action at the time of capturing a determination target image is so determined that images with predetermined actions will be excluded from abnormal-region detection targets to detect an abnormal region only from each of the other images, efficient diagnostic support can be achieved.

Next, a variation of the first Embodiment of the present disclosure will be described. In the first Embodiment mentioned above, the action determination unit 110 makes all of the treatment action determination, the differential action determination, the attentive action determination, and the insertion action determination for each of determination target images. However, all of these action determinations are not necessarily required, and the types of action determinations may be set to be selectable by the operator.

For example, when the subject body is to be observed without any treatment, the treatment action determination is unnecessary. Further, in a phase where the insertion action has been already completed, the insertion action determination is unnecessary. Thus, if the operator selects the types of action determinations made by the action determination unit 110 according to the examination purpose or the phase during the examination, image processing can be performed efficiently.

The types of action determinations to be made can be input with operations to the operation input unit 12. When a signal is input to select one or more action determinations from the operation input unit 12, the action determination unit 110 can cause each determination unit according to the selected type of action determination to perform processing.

Next, the second Embodiment of the present disclosure will be described.

Figure 10:
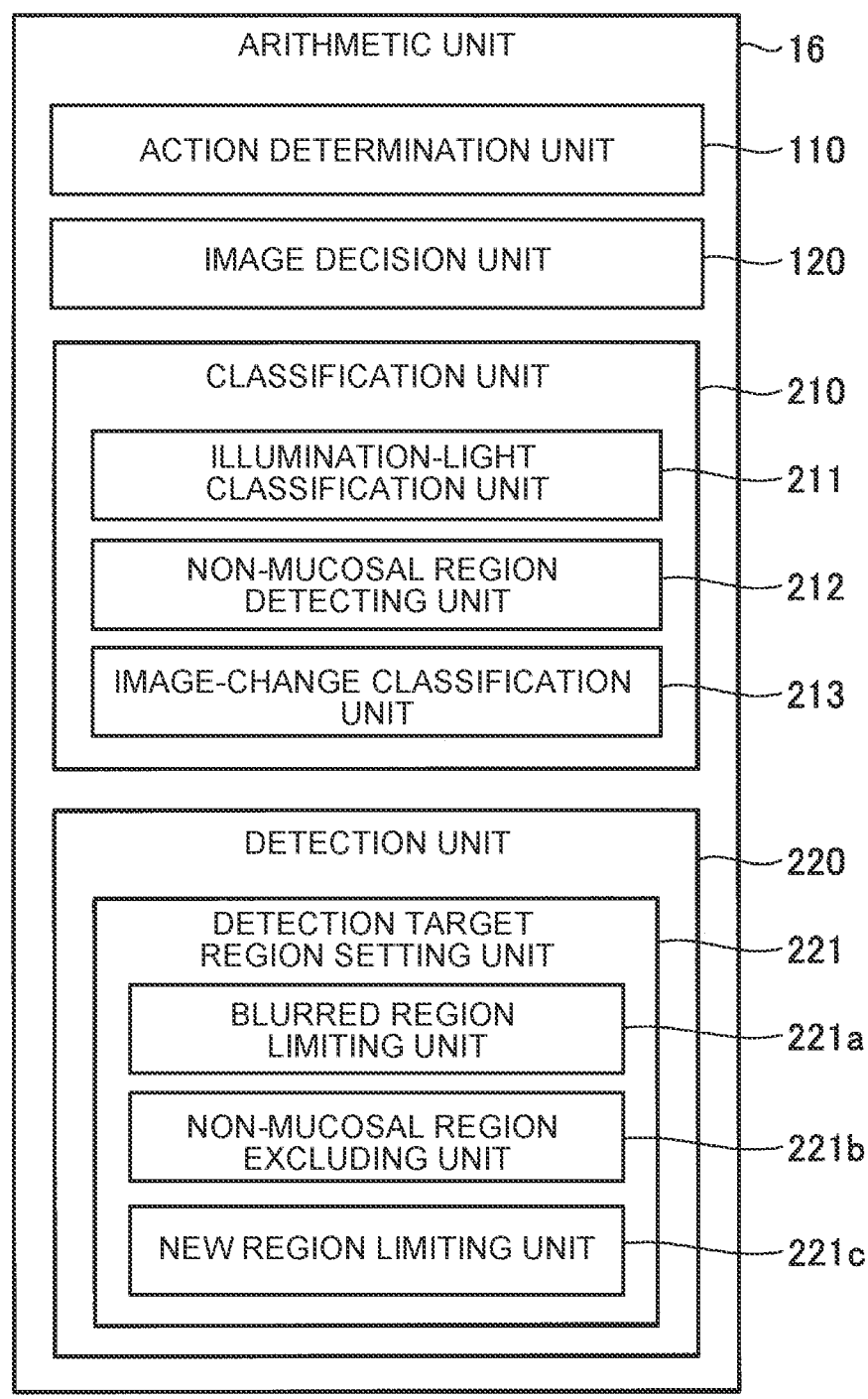
FIG. 10 is a block diagram illustrating the configuration of an arithmetic unit provided in an image processing device according to a second Embodiment of the present disclosure.

FIG. 10 is a block diagram illustrating the configuration of an arithmetic unit provided in an image processing device according to the second Embodiment. The image processing device according to the second Embodiment includes an arithmetic unit 16 illustrated in FIG. 10 instead of the arithmetic unit 15 illustrated in FIG. 1. The configuration and operation of each of the units in the image processing device other than the arithmetic unit 16 are the same as those in the first Embodiment and will not be described again to avoid redundancy.

The arithmetic unit 16 includes an action determination unit 110 that determines an operator's action at the time of capturing a determination target image, an image decision unit 120 that decides on each of detection target images for abnormal regions, a classification unit 210 that classifies the detection target images for the abnormal regions based on predetermined conditions, and a detection unit 220 that performs detection processing on the abnormal regions according to the classification results by the classification unit 210. Among these units, the configurations and operation of the action determination unit 110 and the image decision unit 120 are the same as those in Embodiment 1.

The classification unit 210 has an illumination-light classification unit 211, a non-mucosal region detecting unit 212, and an image-change classification unit 213, and these units classify the detection target images decided by the image decision unit 120 based on respective conditions. Note that the classification unit 210 may have at least one of these units, or may have all of the units.

The illumination-light classification unit 211 classifies detection target images according to the illumination light used during image capturing. Specifically, the detection target images are classified into images captured under incandescent light, and images captured under special light as narrow-band light in a specific wavelength band. Like the special-light determination unit 112c in the differential action determining unit 112, this classification is made based on the average color in the determination target image. The illumination-light classification unit 211 classifies each of images, in which the average color in a target region set in the image is deviated in a direction of green color from a hue distribution in a mucosal region, as each image captured under the special light, and classifies the other images as images captured under normal light.

The non-mucosal region detecting unit 212 performs processing for detecting, from detection target images, regions other than the mucous membrane, i.e., non-mucosal regions such as regions in which treatment tools like forceps, tools like clips, part of the endoscope 2, and the like come out, to classify the detection target images depending on whether such a non-mucosal region is detected. The method of detecting regions in which treatment tools like forceps come out is the same as that of the treatment tool determining unit 111a (see FIG. 3) in the treatment action determining unit 111. The method of detecting regions in which tools like clips come out is the same as that of the treated-region determination unit 113a (see FIG. 5) in the attentive action determining unit 113. The method of detecting regions in which part of the endoscope 2 comes out is the same as that of the back-of-fold checking determination unit 113e (same as above) in the attentive action determining unit 113.

The image-change classification unit 213 classifies the detection target images according to the magnitude of a change in detection target image from an image in a preceding frame. In detail, the image-change classification unit 213 calculates a motion vector between the image and an image preceding by a predetermined number of frames (e.g., the previous frame). Like the movement determination unit 112e (see FIG. 4) in the differential action determining unit 112, the motion vector is calculated by the block matching method for each rectangular region obtained by dividing the image into plurality of rectangular regions.

Then, the image-change classification unit 213 makes classifications by setting, as an amount representing an image change, the number of rectangular regions high in correlation value between images to be compared. In other words, images in which the number of rectangular regions high in correlation value is less than a predetermined number are classified as images with large changes. On the other hand, images in which the number of rectangular regions high in correlation value is more than or equal to the predetermined number are classified as images with small changes. Further, when the images with small changes are continued during a predetermined period along the time series, the image-change classification unit 213 determines, as small-change successive images, images contained during the continuous period.

The detection unit 220 includes a detection target region setting unit 221 that sets a detection target region in each detection target image according to the classification results by the classification unit 210. Depending on the configuration of the classification unit 210, the detection target region setting unit 221 has at least one of a blurred region limiting unit 221a, a non-mucosal region excluding unit 221b, and a new region limiting unit 221c. When the classification unit 210 has all of the illumination-light classification unit 211, the non-mucosal region detecting unit 212, and the image-change classification unit 213, the detection target region setting unit 221 also has all of the blurred region limiting unit 221a, the non-mucosal region excluding unit 221b, and the new region limiting unit 221c.

In each of the detection target images classified by the illumination-light classification unit 211 to be captured under the special light, the blurred region limiting unit 221a limits a detection target region to a region in which a texture structure is blurred.

In each of the detection target images from which non-mucosal regions are detected by the non-mucosal region detecting unit 212, the non-mucosal region excluding unit 221b sets each of regions other than the non-mucosal regions as a detection target region.

In each of the detection target images classified by the image-change classification unit 213 according to the magnitude of a change in detection target image, the new region limiting unit 221c sets the detection target region. Here, the new region means a region newly appearing in the detection target image without being present in any image of a preceding frame, i.e., a region newly coming into view in the direction of movement of the endoscope 2.

Figure 11:
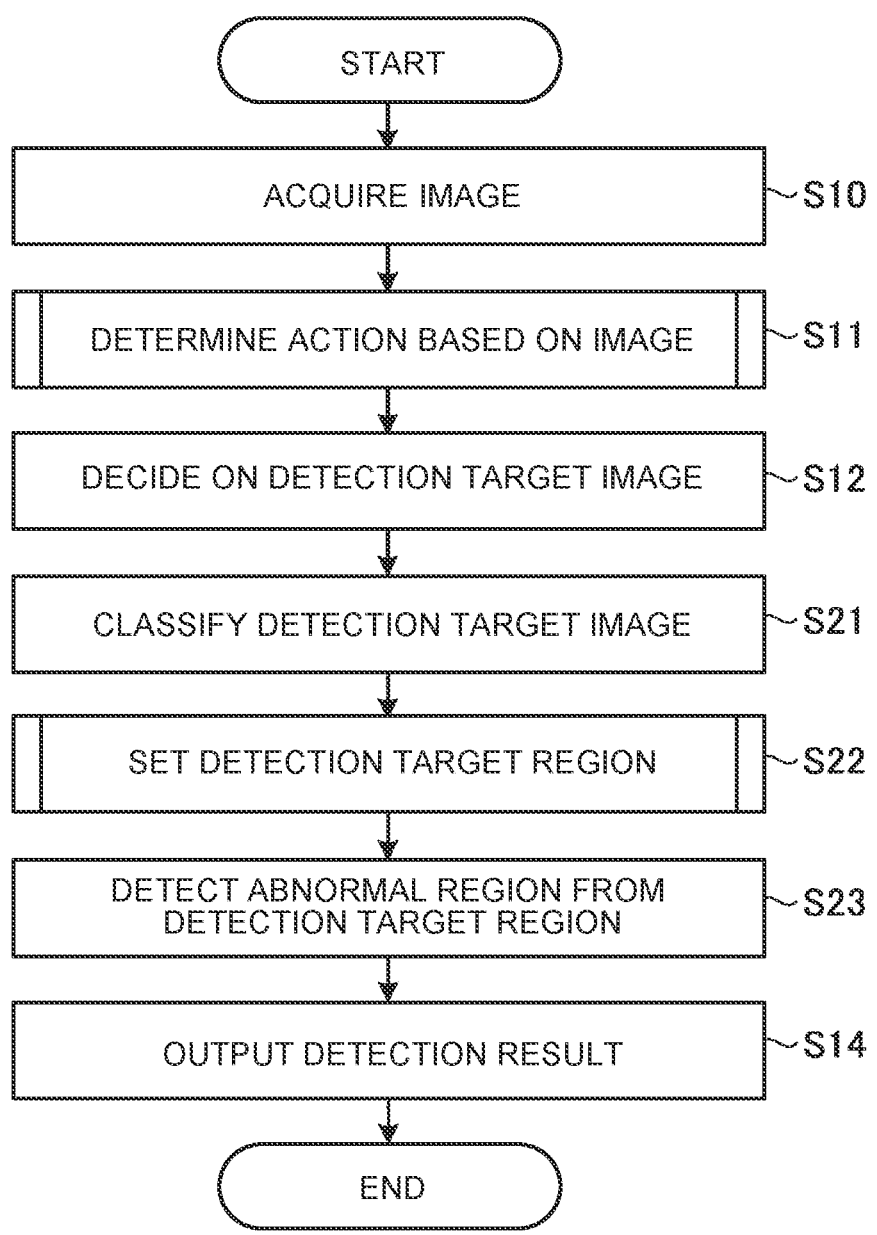
FIG. 11 is a flowchart illustrating an image processing method according to the second Embodiment of the present disclosure.

Next, an image processing method according to the second Embodiment will be described. FIG. 11 is a flowchart illustrating the image processing method according to the second Embodiment. Note that steps S10 to S12 in FIG. 11 are the same as those in Embodiment 1 (see FIG. 8).

In step S21 following step S12, the classification unit 210 classifies detection target images decided in step S12. In Embodiment 2, it is assumed that the classification unit 210 includes all of the illumination-light classification unit 211, the non-mucosal region detecting unit 212, and the image-change classification unit 213, and respective units classify the detection target images, respectively. In other words, the classification as to whether the detection target images are images captured under the special light, the classification as to whether non-mucosal regions are detected from the detection target images, and classification by the magnitude of a change in detection target image from each image in a preceding frame are made.

Figure 12:
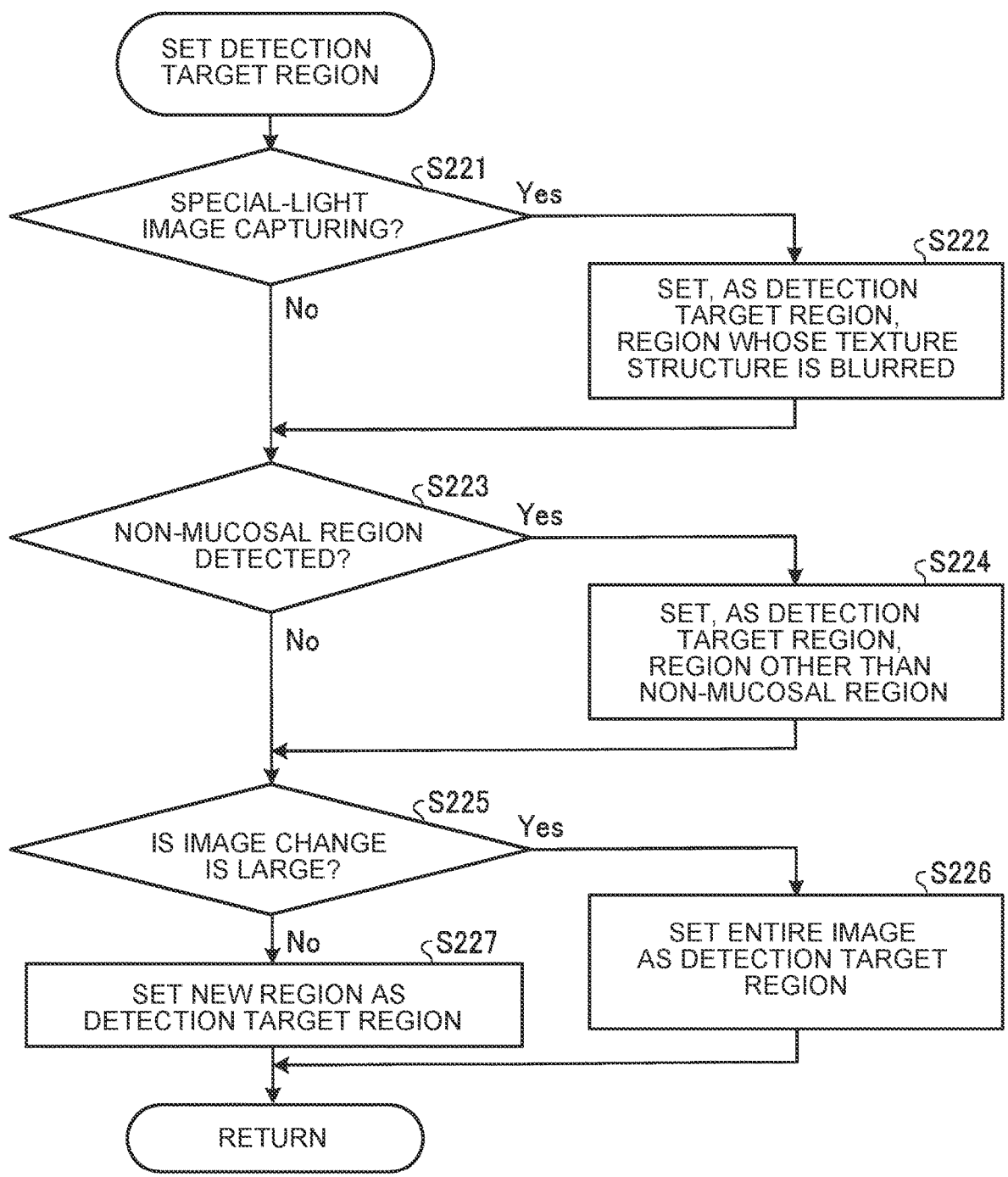
FIG. 12 is a flowchart illustrating the details of detection target region setting processing.

In the following step S22, the detection target region setting unit 221 sets a detection target region based on the classification result of each of the detection target images in step S21. FIG. 12 is a flowchart illustrating the details of detection target region setting processing. In Embodiment 2, it is assumed that the detection target region setting unit 221 includes all of the blurred region limiting unit 221a, the non-mucosal region excluding unit 221b, and the new region limiting unit 221c.

In step S221, the detection target region setting unit 221 determines whether each detection target image is classified as an image captured under the special light. When the detection target image is not classified as the image captured under the special light (No command in step S221), the processing proceeds directly to step S223.

On the other hand, when the detection target image is classified as the image captured under the special light (Yes command in step S221), the blurred region limiting unit 221a sets, as the detection target region, a region in which the texture structure is blurred in the detection target image (step S222).

Here, image capturing under the special light is usually performed to classify the state of the texture structure in the target region during the differential action. Therefore, a region with a blurred texture structure, i.e., a blurred region is considered not to be a differential target. Therefore, in step S222, this blurred region as not being the differential target is set as the detection target region. The blurred region can be extracted by determining whether the contrast of frequency components in the image falls within a range of tolerance levels at the time of the differential action. In other words, a region whose contrast is out of the range of tolerance levels at the time of the differential action is set as the detection target region. After that, the processing proceeds to step S223.

In step S223, the detection target region setting unit 221 determines whether the detection target image is classified as an image in which a non-mucosal region is detected. When the detection target image is not classified as the image in which the non-mucosal region is detected (No command in step S223), the processing proceeds directly to step S225.

On the other hand, when the detection target image is classified as the image in which the non-mucosal region is detected (Yes command in step S223), the non-mucosal region excluding unit 221b sets, as the detection target region, a region other than the non-mucosal region in the detection target image (step S224). Specifically, mask processing is performed on the non-mucosal region. When any other detection target region is already set in step S222, the detection target region is newly added. After that, the processing proceeds to step S225.

In step S225, the detection target region setting unit 221 determines whether the detection target image is classified as an image with a large change. When the detection target image is classified as the image with a large change (Yes command in step S225), the new region limiting unit 221c sets the entire image as the detection target region (step S226). After that, the processing returns to the main routine.

On the other hand, when the detection target image is classified as an image with a small change (No command in step S225), the new region limiting unit 221c sets, as the detection target region, a new region newly appearing in the detection target image (step S227). When any other detection target region is already set in step S222 or S224, the detection target region is newly added.

The position and size of the new region are decided based on the moving direction and moving width obtained by the block matching method from the image-change classification unit 213. In detail, the movement of the endoscope 2 is classified based on the moving directions. Specifically, when a predetermined number of moving directions or more face the same direction, the movement of the endoscope 2 is classified as a translation. When the moving directions face outward from one point as a reference, i.e., when the moving directions are scattered outward from one point, the movement of the endoscope 2 is classified as forward movement. When the moving directions face inward to one point as a reference, i.e., when the moving directions converge toward one point, the movement of the endoscope 2 is classified as backward movement. In the cases of the other patterns, the detection target image is classified as an image with no new region detected, and handled in the same way as the image with a large change.

Then, the position and size of a new region are estimated from the moving direction and moving width. Specifically, when the movement of the endoscope 2 is classified as the translation, the position of the new region is any of four directions of the image ends (up, down, right, and left), which is decided by the direction of a moving direction on the base end side, i.e., by the direction of a departure point of the movement. For example, when the moving direction goes from the lower left toward the upper right, the position of the new region is the left end and lower end of the image. Further, the size of the new region is decided by the size of each of components obtained by decomposing a vector of the moving direction having the moving width as a vector quantity into components in the direction of the position of the new region.

When the movement of the endoscope 2 is classified as forward movement, the position of the new region is the above one point on which the moving directions on the base end side converge, and the size of the new region is decided by the moving width. When the movement of the endoscope 2 is classified as backward movement, the position of the new region is all of the four directions of the image ends, and the size of the new region is decided by the moving width. After that, the processing returns to the main routine.

In step S23 following step S22, the detection unit 220 detects an abnormal region from among detection target regions set in step S22. The processing for detecting the abnormal region is the same as that in Embodiment 1 (see step S13 in FIG. 8) except that the detection target is limited to the detection target region. The following step S14 is the same as in the first Embodiment.

As described above, according to the second Embodiment, since the abnormal-region detection target images decided based on the operator's action at the time of capturing each image are further classified based on the operator's action to narrow down the abnormal-region detection target images, more efficient image processing can be performed.

Next, the third Embodiment of the present invention will be described.

Figure 13:
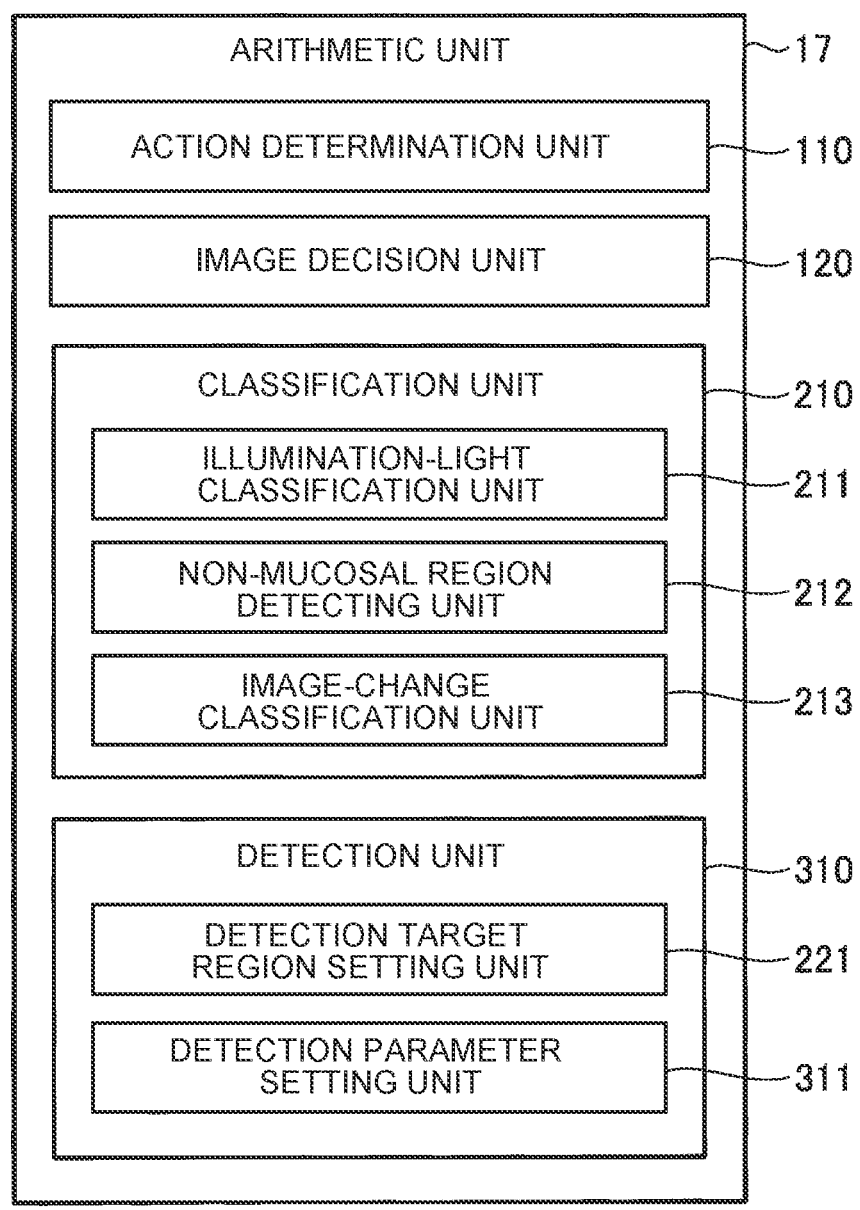
FIG. 13 is a block diagram illustrating the configuration of an arithmetic unit provided in an image processing device according to a third Embodiment of the present disclosure.

FIG. 13 is a block diagram illustrating the configuration of an arithmetic unit provided in an image processing device according to the third Embodiment. The image processing device according to the third Embodiment includes an arithmetic unit 17 illustrated in FIG. 13 instead of the arithmetic unit 15 illustrated in FIG. 1. The configuration and operation of each of the units in the image processing device other than the arithmetic unit 17 are the same as those in the first Embodiment.

The arithmetic unit 17 includes a detection unit 310 having a detection parameter setting unit 311 in addition to a detection target region setting unit 221 as in the arithmetic unit 16 illustrated in FIG. 10. The configuration of each of the units other than the detection parameter setting unit 311 in the arithmetic unit 17 is the same as that in the second Embodiment.

According to the results of classification made by the classification unit 210 for the detection target images decided by the image decision unit 120, the detection parameter setting unit 311 sets detection parameters used in abnormal-region detection processing for the detection target regions set by the detection target region setting unit 221.

Next, an image processing method according to the third Embodiment will be described.

Figure 14:
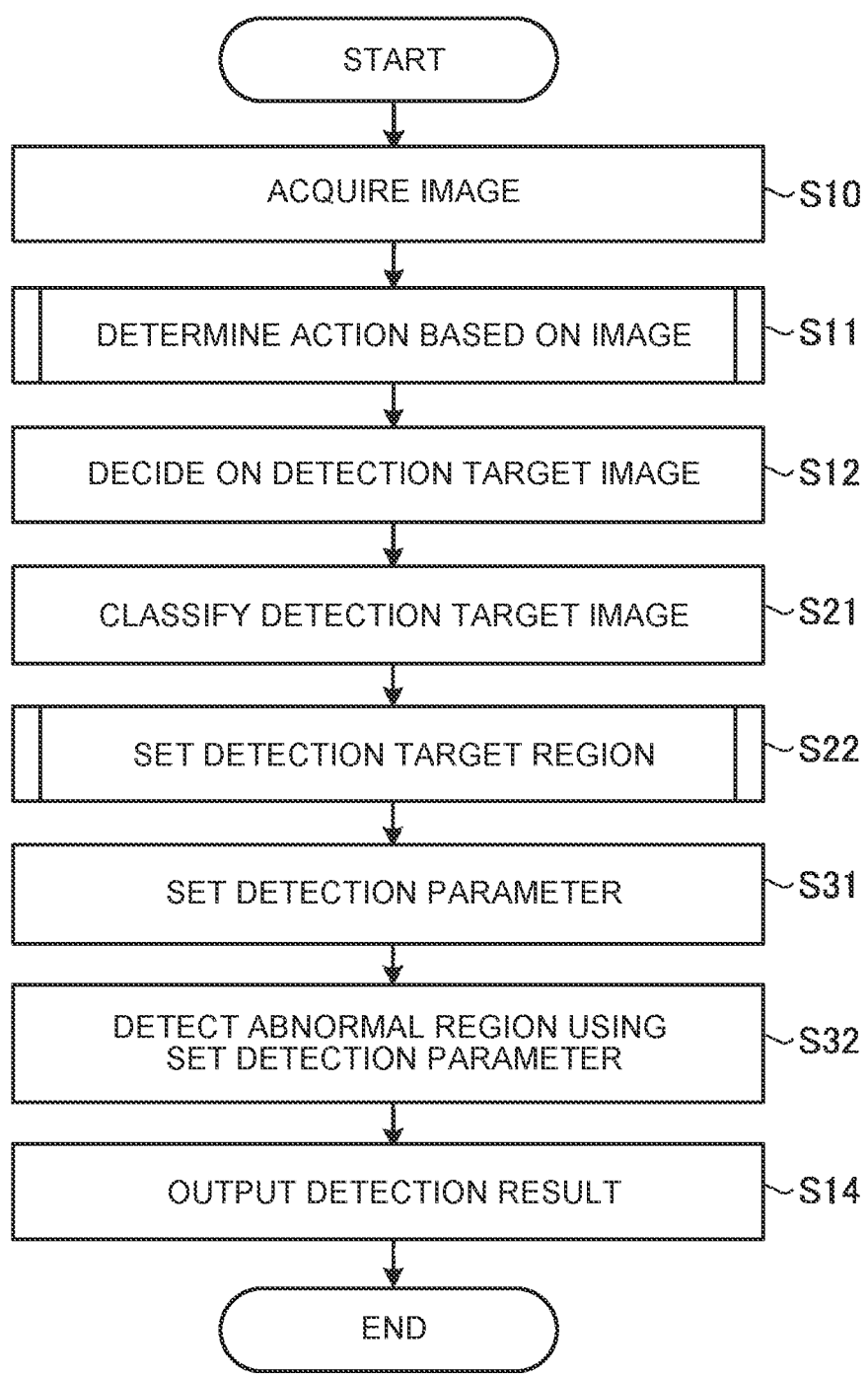
FIG. 14 is a flowchart illustrating an image processing method according to the third Embodiment of the present disclosure.

FIG. 14 is a flowchart illustrating the image processing method according to the third Embodiment. Note that steps S10 to S22 in FIG. 14 are the same as that described in the second Embodiment (see FIG. 11) and will not be described again to avoid redundancy.

In step S31 following step S22, the detection parameter setting unit 311 sets detection parameters in detecting an abnormal region from each of the detection target regions set in step S22 based on the classification results in step S21. Here, the detection parameters include identification boundaries in the feature space of feature values representing abnormal regions, a distribution model of the feature values of the abnormal regions, discriminant functions, representative distribution patterns, and the like. Such detection parameters are created in advance by using teacher data according to the variations possibly classified by the classification unit 210, and stored in the storage unit 14.

As a specific example, when a region with a sharp texture structure is set as a detection target region from among the images captured under the special light and the classified detection target images (see step S222 in FIG. 12), detection parameters created based on a color distribution model of the special light different from normal light are read from the storage unit 14, and set for the detection target region. When a mucosal region obtained by removing non-mucosal regions is set as the detection target region (see step S224 in FIG. 12), detection parameters created based on a color distribution model of the mucous membrane under normal light are read and set from the storage unit 14. Further, when a region in which two or more image capturing situations such as a mucosal region and a new region simultaneously occur is set as the detection target region, detection parameters created based on teacher data corresponding to these image capturing situations are read and set from the storage unit 14.

The present disclosure is not limited to the three embodiments and the variation thereof, and various disclosure can be formed by appropriately combining plurality of components disclosed in the respective embodiments and the variation. For example, some components may be eliminated from all the components illustrated in each embodiment or the variation thereof, or components illustrated in different embodiments and the variation thereof may be combined appropriately.

A medical system comprising an endoscope, a light source being configured to be attached to the endoscope; and an image processing device being in electrical communication with the endoscope to manipulate and to produce images captured by the endoscope in accordance to an action taken by an operator of the endoscope and wherein the image processing device having at least one processor configured to determine, differentiate, classify and to decide whether one or more images captured by the endoscope being suitable for diagnostic purposes and to alert the operator of the endoscope to incorporate one or more images that were missed by the operator.

The at least one processor of the image processing device configured to perform an action determination step that determines, based on an image captured by an endoscope inserted into a subject body, the action of the operator on the endoscope at a time of capturing the image. Next step by the processor is the image decision step that decides whether the image is set as a detection target image for a specific region based on the determination result by the action determination unit. Finally, the processor performs a detection step that detects the specific region from the detection target image.

Within the action determination step, a treatment action determines whether the operator's action at the time of capturing the image is a treatment action to conduct on the subject body a treatment. The treatment action has a treatment tool that detects, from the image, a tube-shaped region, in which the brightness is higher than a threshold value, as a treatment tool region. When the treatment tool detects the region, the operator's action at the time of capturing the image is determined to be the treatment action. The treatment action has a washing action that detects, from the image, a region, which exhibits a specular reflection and in which the time change in area and the position is large, as a washed region, and when the washing action detects the washed region, the operator's action at the time of capturing the image is determined to be the treatment action.

Within the action determination step, a differential action determines whether the operator's action at the time of capturing the image is a differential action to differentiate any portion in the image. The differential action further includes an enlargement determination that determines whether the image is an enlarged image captured by bringing a distal end of the endoscope close to a subject at a predetermined distance or less. when the enlargement determination determines that the image is the enlarged image, then the operator's action at the time of capturing the image is determined to be the differential action.

The differential action has a dyeing determination that determines whether the image is a dyed image obtained by capturing a dyed subject. When the dyeing determination determines that the image is the dyed image, the operator's action at the time of capturing the image is determined to be the differential action.

The differential action further includes a special-light determination that determines whether the image is a special-light image captured using special light. When the special-light determination determines that the image is the special-light image, the operator's action at the time of capturing the image is determined to be the differential action.

The differential action further includes a front-view determination that determines whether the image is a front-view image obtained by capturing a subject from the front view. When the front-view determination determines that the image is the front-view image, the operator's action at the time of capturing the image is determined to be the differential action.

The differential action further includes a movement determination that determines whether the image is an image with less movement, in which an amount representing movement of a structure corresponding to that of an image preceding by a predetermined number of frames is less than or equal to a threshold value. The image with less movement is then captured continuously during a certain fixed period or more prior to the image. when the movement determination determines that the image is the image with less movement and the image with less movement is captured continuously during the certain fixed period or more prior to the image, then the operator's action at the time of capturing the image is determined to be the differential action.

Within the action determination step, the action determination includes an attentive action that determines whether the operator's action at the time of capturing the image is an attentive action to pay close attention to a subject body under examination.

The attentive action has a treated-region that detects, from the image, a tube-shaped region having a color different from that of a mucosal region, and a bleeding region. When the treated-region detects the tube-shaped region and the bleeding region, the operator's action at the time of capturing the image is determined to be the attentive action.

The attentive action has a front-view determination that determines whether the image is a front-view image obtained by capturing a subject from the front view. When the front-view determination determines that the image is the front-view image, the operator's action at the time of capturing the image is determined to be the attentive action.

The attentive action has a close-up determination that determines whether the image is a close-up image to capture a region in which the distance from a distal end of the endoscope is less than or equal to a predetermined value. When the close-up determination determines that the image is the close-up image, the operator's action at the time of capturing the image is determined to be the attentive action.

The attentive action has a movement determination that determines whether the image is an image with less movement, in which an amount representing movement of a structure corresponding to that of an image preceding by a predetermined number of frames is less than or equal to a threshold value. The image with less movement is captured continuously during a certain fixed period or more prior to the image.

When the movement determination determines that the image is the image with less movement and the image with less movement is captured continuously during the certain fixed period or more prior to the image, then the operator's action at the time of capturing the image is determined to be the attentive action.

When the attentive action detects, from the image, an endoscope region in which part of the endoscope comes out, and when the endoscope region is detected from the image, then the operator's action at the time of capturing the image is determined to be the attentive action.

The action determination includes an insertion action that determines whether the operator's action at the time of capturing the image is an insertion action to insert the endoscope into the subject body. The insertion action has a forward-path feature that determines whether the endoscope inserted from the anus of the subject body is moving in the forward path from the large intestine toward the appendix of the subject body. When the forward-path feature determines that the endoscope is moving in the forward path, the operator's action at the time of capturing the image is determined to be the insertion action.

The insertion action has a moving-direction feature that determines in which direction the endoscope is moving, to a distal end or a base end of the endoscope. When the moving-direction determines that the endoscope is moving toward the distal end of the endoscope, the operator's action at the time of capturing the image is determined to be the insertion action.

When the operator's action at the time of capturing the image is a predetermined action, the image is not set as the detection target image for the specific region.

An operation input step is used to input information to the image processing device in which the image decision step sets the predetermined action based on the information input from the operation input step.

A classification feature classifies the detection target image based on predetermined conditions. The detection step includes a detection target region setting feature that sets a detection target region for the specific region in the detection target image according to the classification result by the classification feature.

The classification feature has an illumination-light that classifies the detection target image according to the type of illumination light at the time of image capturing. The detection target region setting feature sets the detection target region based on the contrast of a frequency component of a detection target image which is so classified that illumination light at the time of image capturing is special light.

The classification feature has a non-mucosal region detecting feature that detects a non-mucosal region from the detection target image. The detection target region setting then sets as the detection target region, a region other than the non-mucosal region in the detection target image from which the non-mucosal region is detected.

The classification feature has an image-change classification feature that classifies the detection target image according to the magnitude of a change in the detection target image from an image proceeding by a predetermined number of frames. The detection target region setting then sets as the detection target region which the entire detection target image classified as being large in change, and sets, as the detection target region, a new region appearing in a detection target image classified as being small in change and without being present in an image of a preceding frame.

The image processing device includes a detection parameter setting feature that sets a detection parameter used to detect the specific region from the detection target region according to the classification result by the classification unit.

One aspect of the present disclosure is directed to an endoscope system having an image processing device as described hereinabove and an endoscope.

Another aspect of the present disclosure is directed to an image processing method comprising an action determination step for causing an arithmetic unit to determine, based on an image captured by an endoscope inserted into a subject body, an operator's action on the endoscope at a time of capturing the image. Next, an image decision step is causing the arithmetic unit to decide whether the image is set as a detection target image for a specific region based on the determination result in the action determination step. Finally, a detection step is causing the arithmetic unit to detect the specific region from the detection target image.

A further aspect of the present disclosure is directed to an image processing device having one or more processors using one or more programs to execute an action determination step of determining, based on an image captured by an endoscope inserted into a subject body, an operator's action on the endoscope at a time of capturing the image and an image decision step of deciding whether the image is set as a detection target image for a specific region based on the determination result in the action determination step and a detection step of detecting the specific region from the detection target image.

While various features are presented hereinabove, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. An image processing device comprising:
   at least one processor configured to:
      determine whether an operator's action in operating an endoscope inserted into a subject body is a predetermined action based on an image captured by the endoscope inserted into the subject body;
      in response to determining that the operator's action is not the predetermined action, designate the image captured by the endoscope inserted into the subject body as a detection target image; and
      detect a specific region from the detection target image,
   wherein the predetermined action is a treatment action to give the subject body a treatment, and
   wherein in determining whether the operator's action is the treatment action, the processor is configured to:
      detect, from the image, a region, which exhibits a specular reflection and whose time change in area and position is larger than a threshold value, as a washed region; and
      in response to detecting the washed region, determine that the operator's action is the treatment action.

2. The image processing device according to claim 1, wherein the predetermined action is a differential action to differentiate any portion in the image.

3. The image processing device according to claim 2, wherein the at least one processor is configured to, in determining whether the operator's action is the predetermined action:
   determine whether the image is a dyed image obtained by capturing a dyed subject; and
   in response to determining that the image is not the dyed image, determine that the operator's action is not the differential action.

4. The image processing device according to claim 2,
wherein the at least one processor is configured to, in determining whether the operator's action is the predetermined action:
   determine whether the image is a special-light image captured using special light; and
   in response to determining that the image is not the special-light image, determine that the operator's action is not the differential action.

5. The image processing device according to claim 2,
wherein the at least one processor is configured to, in determining whether the operator's action is the predetermined action:
   determine whether the image is a front-view image obtained by capturing a subject from a front view; and
   in response to determining that the image is not the front-view image, determine that the operator's action is not the differential action.

6. The image processing device according to claim 1,
wherein the predetermined action is an attentive action to pay close attention to a subject.

7. The image processing device according to claim 6,
wherein the at least one processor is configured to, in determining whether the operator's action is the predetermined action:
   determine, from the image, whether a tube-shaped region having a color different from that of a mucosal region, and a bleeding region is detected; and
   in response to determining that the tube-shaped region is not detected, determine that the operator's action is not the attentive action.

8. The image processing device according to claim 6,
wherein the at least one processor is configured to, in determining whether the operator's action is the predetermined action:
   determine, whether the image is a front-view image obtained by capturing a subject from a front view; and
   in response to determining that the image is not the front-view image, determine that the operator's action is not the attentive action.

9. The image processing device according to claim 6,
wherein the at least one processor is configured to, in determining whether the operator's action is the predetermined action:
   determine, whether the image is a close-up image to capture a region whose distance from a distal end of the endoscope is less than or equal to a predetermined value; and
   in response to determining that the image is not the close-up image, determine that the operator's action is not the attentive action.

10. The image processing device according to claim 6,
wherein the at least one processor is configured to, in determining whether the operator's action is the predetermined action:
   determine, whether the image is an image with less movement, in which an amount representing movement of a structure corresponding to that of an image preceding by a predetermined number of frames is less than or equal to a threshold value, and the image with less movement is captured continuously during a certain fixed period or more prior to the image; and
   in response to determining that the image is not the image with less movement, determine that the operator's action is not the attentive action.

11. The image processing device according to claim 6,
wherein the at least one processor is configured to, in determining whether the operator's action is the predetermined action:
   determine, from the image, whether an endoscope region in which part of the endoscope comes out is detected; and
   in response to determining that the endoscope region is not detected, determine that the operator's action is not the attentive action.

12. The image processing device according to claim 1,
wherein the predetermined action is an insertion action to insert the endoscope into the subject body.

13. The image processing device according to claim 12,
wherein the at least one processor is configured to, in determining whether the operator's action is the insertion action:
   determine, from the image, whether the endoscope inserted from an anus of the subject body is moving in a forward path from a large intestine toward an appendix of the subject body, is detected; and
   in response to determining that the endoscope is not moving in the forward path, determine that the operator's action is not the insertion action.

14. The image processing device according to claim 12,
wherein the at least one processor is configured to, in determining whether the operator's action is the insertion action:
   determine, from the image, in which direction the endoscope is moving, to a distal end or a base end of the endoscope, and
   in response to determining that the endoscope is moving to the base end, determine that the operator's action is not the insertion action.

15. An image processing device comprising:
at least one processor configured to:
   determine whether an operator's action in operating an endoscope inserted into a subject body is a predetermined action based on an image captured by the endoscope inserted into the subject body;
   in response to determining that the operator's action is not the predetermined action, designate the image captured by the endoscope inserted into the subject body as a detection target image;
   classify the detection target image based on predetermined conditions;
   set a detection target region in the detection target image according to a result of classifying the detection target image; and
   detect a specific region from the detection target region in the detection target image set.

16. The image processing device according to claim 15,
wherein the predetermined conditions include whether contrast of frequency components in the detection target image falls within a range of tolerance levels, and
wherein the at least one processor is configured to set a region in the detection target image having the contrast of frequency components that falls out of the range of tolerance levels as the detection target region.

17. The image processing device according to claim 15,
wherein the at least one processor is configured to:
   detect a non-mucosal region from the detection target image;
   set a region in the detection target image other than the non-mucosal region in the detection target image as a detection target region; and detect the specific region from the detection target region in the detection target image set.

18. The image processing device according to claim 15, wherein the at least one processor is configured to:
    classify a change in the detection target image as being large or small according to a magnitude of a change in the detection target image from an image preceding by a predetermined number of frames;
    in response to classifying the change in the detection target image as being large, set a whole of the detection target image as the detection target region; and
    in response to classifying the change in the detection target image as being small, set a new region appearing in the detection target image without being present in the image preceding by the predetermined number of frames as the detection target region.

19. The image processing device according to claim 15, wherein the at least one processor is configured to:
    set a detection parameter used to detect the specific region from the detection target region according to the result of classifying the detection target image.

20. The image processing device according to claim 15, wherein the predetermined action is at least one of a treatment action, a differential action, an attentive action and insertion action.

21. The image processing device according to claim 15, wherein the predetermined action is at least one of:
    a treatment action that gives a medical treatment to the subject body;
    a differential action that differentiates any portion in the image;
    an attentive action that pays close attention to the subject body; and
    an insertion action that inserts the endoscope into the subject body.

22. The image processing device according to claim 21, wherein the predetermined action is the treatment action.

23. The image processing device according to claim 22, wherein the at least one processor is configured to determine that the operator's action is the treatment action when a treatment tool region is detected in the image.

24. The image processing device according to claim 22, wherein the at least one processor is configured to determine that the operator's action is the treatment action when a washed region is detected in the image.

25. The image processing device according to claim 15, wherein the at least one processor is configured to:
    in response to determining that the operator's action is the predetermined action, not designate the image as the detection target image.

26. The image processing device according to claim 15, wherein the at least one processor is configured to:
    receive information input by a user; and
    set a type of the predetermined action based on the information input by the user.

* * * * *